(12) United States Patent
Kita et al.

(10) Patent No.: US 7,736,602 B1
(45) Date of Patent: Jun. 15, 2010

(54) MERCURY MONITORING SYSTEM AND REACTION CHAMBER FOR ENHANCING CONVERSION OF ELEMENTAL MERCURY GAS INTO OXIDIZED MERCURY

(75) Inventors: Dieter Kita, Blackstone, MA (US); Jeffrey Socha, Berlin, MA (US); Bryan A. Marcotte, Blackstone, MA (US)

(73) Assignee: Thermo Fisher Scientific Inc., Waltham, MA (US)

(*) Notice: Subject to any disclaimer, the term of this patent is extended or adjusted under 35 U.S.C. 154(b) by 38 days.

(21) Appl. No.: 11/818,664

(22) Filed: Jun. 14, 2007

(51) Int. Cl.
*B01J 19/00* (2006.01)
*G01N 21/00* (2006.01)

(52) U.S. Cl. .................. 422/187; 422/189; 422/198; 422/218; 422/222; 422/109; 422/110; 422/83; 73/1.02; 73/1.03; 73/1.06; 73/23.31

(58) Field of Classification Search .............. None
See application file for complete search history.

(56) References Cited

U.S. PATENT DOCUMENTS

| | | | | |
|---|---|---|---|---|
| 3,334,513 A | * | 8/1967 | Thomas ................ 73/31.04 |
| 5,089,134 A | * | 2/1992 | Ando et al. ............. 210/496 |
| 5,114,447 A | * | 5/1992 | Davis .................... 55/485 |
| 2005/0084976 A1 | * | 4/2005 | Baldwin et al. ......... 436/81 |
| 2006/0096926 A1 | * | 5/2006 | Mazyck et al. .......... 210/663 |
| 2008/0282764 A1 | * | 11/2008 | Holt et al. .............. 73/1.03 |

* cited by examiner

*Primary Examiner*—Jennifer A Leung
(74) *Attorney, Agent, or Firm*—Chapin IP Law, LLC; Barry W. Chapin, Esq.

(57) ABSTRACT

A reaction chamber enables a reaction between received elemental mercury gas and an oxidizing agent gas. The reaction chamber includes a porous (or permeable) medium through which to pass the elemental mercury gas and the oxidizing agent gas. Passing of the elemental mercury gas and the oxidizing agent gas through the porous medium supports a number of useful functions. For example, the porous medium enhances mixing of the elemental mercury gas with the oxidizing agent gas to enhance a reaction. Also, the porous medium increases an amount of surface area in a reaction chamber on which reactions (e.g., heterogeneous surface reactions) can take place between the elemental mercury gas and the oxidizing agent gas to form oxidized mercury gas. Accordingly, the reaction chamber configured to include a porous medium enhances a conversion of elemental mercury gas into oxidized mercury gas.

25 Claims, 21 Drawing Sheets

MERCURY MONITORING SYSTEM AND REACTION CHAMBER FOR ENHANCING CONVERSION OF ELEMENTAL MERCURY GAS INTO OXIDIZED MERCURY

BACKGROUND

Emissions from fossil fuel combustion facilities, such as flue gases of coal-fired utilities and municipal solid waste incinerators, typically include mercury. For example, emissions as a result of such operations can include vaporized mercury as elemental mercury, $Hg^0$, and/or mercury-based compounds (e.g., an oxidized form of mercury ($Hg^{+2}$), such as mercuric chloride or mercuric nitrate).

Many countries regulate emissions of mercury in waste gases because of potential environmental hazards posed by mercury emissions. Facilities that generate gas emissions containing mercury typically utilize a mercury monitoring system to measure total mercury concentration in the emissions to comply with the regulations. As mentioned above, the emissions can include element mercury and/or oxidized mercury.

Certain mercury monitoring systems include a converter that converts the oxidized mercury in a sample emission into elemental mercury, such as by using a mercury converter performing a thermal conversion or cracking process. The mercury monitoring system then measures the total amount or concentration of elemental mercury in the emission using an analyzer, such as an atomic fluorescence spectrometer.

To ensure accurate measurement of the elemental mercury concentration in the emissions, mercury monitoring systems typically include a calibration assembly. The calibration assembly provides vaporized elemental mercury to the analyzer at a particular concentration level to calibrate the mercury monitoring system. After calibration, the mercury monitoring system can be used to measure an amount of mercury present in a gas sample collected from an active smokestack.

SUMMARY

Conventional mercury calibration systems can combine elemental mercury gas with an oxidizing agent gas to produce an oxidized mercury gas used for calibration purposes. One hurdle associated with producing an oxidized mercury gas sample is the relatively difficult task of reacting the elemental mercury gas with the oxidizing agent gas to produce the oxidized mercury gas sample for calibration of a mercury monitoring system. As mentioned, certain conventional methods include merely providing an elemental mercury gas and an oxidizing agent gas in a chamber to produce oxidized mercury. However, mere presence of elemental mercury gas and an oxidizing agent gas in a chamber may not yield a high enough quantity of oxidized mercury for the gas sample (and at a fast enough rate) because only a small quantity of the elemental mercury gas and oxidizing agent gas in the chamber may react to form oxidized mercury gas. Such a quantity may be too small (or produced too slowly) for calibrating the mercury monitoring system.

Embodiments herein include a novel reaction chamber for enhancing a conversion of elemental mercury gas into an oxidized mercury gas. For example, according to one embodiment, a mercury monitoring system includes a reaction chamber to carry out a reaction between received elemental mercury gas and an oxidizing agent gas. The reaction chamber includes a porous (or permeable) medium through which to pass the elemental mercury gas and the oxidizing agent gas to produce an oxidized mercury gas sample used to calibrate a mercury monitoring system.

Passing of the elemental mercury gas and the oxidizing agent gas through the porous medium of the reaction chamber supports a couple of functions. First, use of the porous medium in the reaction chamber enhances mixing of the elemental mercury gas with the oxidizing agent gas to enhance a reaction. Second, use of the porous medium according to embodiments herein increases an amount of surface area in a reaction chamber on which reactions (e.g., heterogeneous surface reactions) can take place between the elemental mercury gas and the oxidizing agent gas to form oxidized mercury gas. Accordingly, use of porous medium (e.g., metal such as sintered stainless steel, ceramic, etc.) in a reaction chamber can substantially increase an amount of surface area to carry out a reaction without substantially increasing a size of the chamber so that it is prohibitively large. Thus, the porous medium can be relatively compact in size (e.g., occupy a reasonable volume of space) yet provide a relatively large surface area for carrying out a reaction.

Note that use of the porous medium in the reaction chamber as discussed above need not always result in conversion of an entire quantity of received elemental mercury gas into oxidized mercury. For example, in addition to emitting oxidized mercury gas, the reaction chamber can emit an unreacted portion of received oxidizing agent as well as an unreacted portion of received elemental mercury gas. In certain test environments, it is desirable that the sample emitted from the chamber includes a portion of oxidized mercury gas as well as a portion of unreacted elemental mercury gas passed through the reaction chamber. Limiting the amount of oxidizing agent gas supplied to the reaction chamber can help to limit an amount of elemental mercury gas converted into oxidized mercury gas.

In one embodiment, the porous medium has a nominal pore size in a range between 0.1 micrometers and 500 micrometers, although the porous media can have any acceptable pore size for enhancing a conversion of elemental mercury gas into oxidized mercury gas. According to certain embodiments, the nominal pore size of the porous medium can range between 1 and 100 micrometers.

Additionally, embodiments herein include one or more heaters in thermal communication with the chamber to heat the received elemental mercury gas and the oxidizing agent gas in the chamber prior to passing of the elemental mercury gas and the oxidizing agent gas through the porous medium. A controller can be used to regulate a temperature of the one or more heaters. Heating the reaction chamber and gas therein to a temperature value in a range between 40 and 600 deg Celsius reduces a likelihood that the mercury will stick to the walls of the chamber or pores of the porous medium as it passes through the reaction chamber. Application of heat also can enhance a reaction of the elemental mercury gas and the oxidizing agent gas into oxidized mercury gas.

In addition to inclusion of a heater, embodiments herein can include use of a humidifier to modify a relative humidity of the elemental mercury gas prior to being received by the reaction chamber. Humidifying the mercury calibration gas sample and/or the elemental mercury gas prior to entering the reaction chamber enhances a flow of the mercury gas through the channels of the mercury monitoring system. In other words, adding water to the mercury can reduce a likelihood that the mercury will stick to surface areas associated with the reaction chamber as well as other channels in the mercury monitoring system.

One particularly useful application of the reaction chamber according to embodiments herein is a mercury monitoring system used for testing a presence of mercury as mentioned. Under proper conditions, the reaction chamber (including the porous medium) provides a way to substantially convert most or, if so desired, nearly all received elemental mercury gas into oxidized mercury gas. Assuming that the amount of elemental mercury gas supplied to the chamber is delivered at a relatively constant rate, the amount of oxidized mercury gas produced by the reaction chamber can be controlled by limiting an amount of oxidizing agent gas supplied to the reaction chamber.

Some embodiments herein include repeatedly switching between delivery of the gas sample produced by the reaction chamber and porous medium on a first path (including an oxidized mercury gas-to-elemental mercury gas converter) and second flow path (not including the converter) to verify at least one of: i) an ability of an elemental mercury detector in a mercury monitoring system to properly detect a presence of elemental mercury gas in a sample, and ii) an ability of a converter in the mercury monitoring system to convert oxidized mercury gas into elemental mercury gas. As will be discussed later in this specification, passing the integrity checks according to embodiments herein provides an assurance that the mercury monitoring system can properly detect a presence of mercury in a flue gas sample.

Techniques herein are well suited for use in applications such as those supporting a reaction between a received elemental mercury gas and an oxidizing agent gas to produce an oxidized mercury gas sample. However, it should be noted that configurations herein are not limited to such use and thus configurations herein and deviations thereof are well suited for use in other environments as well.

Note that each of the different features, techniques, configurations, etc. discussed herein can be executed independently or in combination. Accordingly, the present invention can be embodied and viewed in many different ways.

Also, note that this summary section herein does not specify every embodiment and/or incrementally novel aspect of the present disclosure or claimed invention. Instead, this summary only provides a preliminary discussion of different embodiments and corresponding points of novelty over conventional techniques. For additional details and/or possible perspectives (permutations) of the invention, the reader is directed to the Detailed Description section and corresponding figures of the present disclosure as further discussed below.

BRIEF DESCRIPTION OF THE DRAWINGS

The foregoing and other objects, features and advantages of the methods and apparatus will be apparent from the following description of particular embodiments, as illustrated in the accompanying drawings in which like reference characters refer to the same parts throughout the different views. The drawings are not necessarily to scale, emphasis instead being placed upon illustrating the principles of the apparatus.

DETAILED DESCRIPTION

Embodiments herein include a novel reaction chamber (approach) for enhancing conversion of elemental mercury gas into oxidized mercury. For example, according to one embodiment, a mercury monitoring system includes a reaction chamber to enhance a reaction between received elemental mercury gas and an oxidizing agent gas to produce an oxidized mercury gas sample.

According to one embodiment, the reaction chamber includes a porous (or permeable) medium through which to pass the elemental mercury gas and the oxidizing agent gas. Passing of the elemental mercury gas and the oxidizing agent gas through the porous medium supports a couple of functions. First, the porous medium enhances mixing of the elemental mercury gas with the oxidizing agent gas to enhance a reaction. Second, the porous medium increases an amount of surface area in the reaction chamber on which reactions (e.g., heterogeneous surface reactions) can take place between the elemental mercury gas and the oxidizing agent gas to form oxidized mercury gas. Use of the porous medium (e.g., metal such as sintered stainless steel, ceramic, etc.) in a reaction chamber can substantially increase an amount of surface area in the chamber to carry out a reaction without substantially increasing a size of the chamber so that it is prohibitively large. In other words, the porous medium can be relatively compact in size (e.g., occupy a reasonable volume of space), yet provide a relatively large surface area for carrying out and enhancing a reaction.

Figure 1:
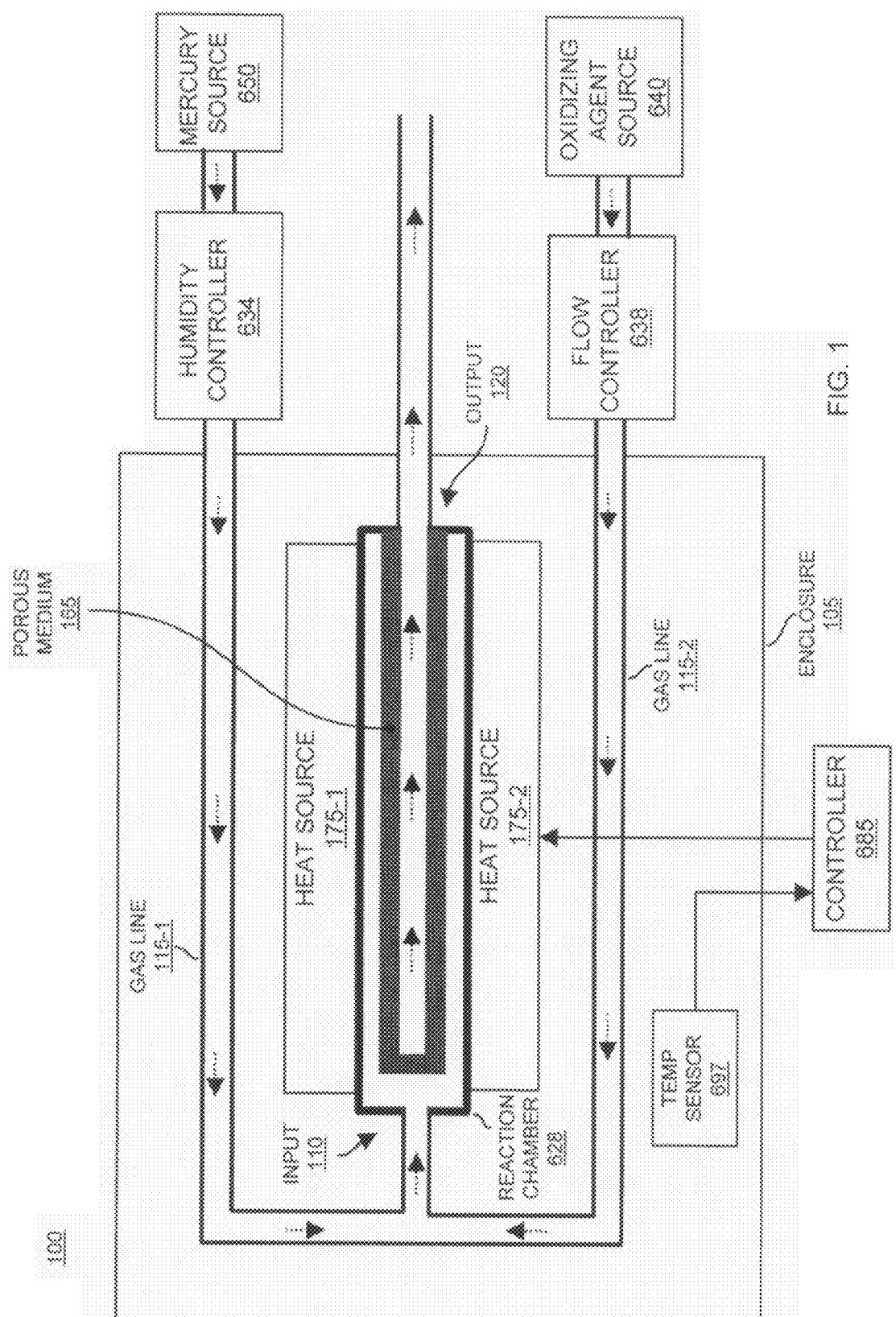
FIG. 1 is a diagram of a reaction chamber for enhancing a reaction between elemental mercury gas and an oxidizing agent gas according to embodiments herein.

FIG. 1 is a (cross-section) diagram of a gas generator system 100 according to embodiments herein. As shown, gas generator system 100 includes mercury source 650 (e.g., an elemental mercury gas source), oxidizing agent source 640 (e.g., a chlorine gas source), humidity controller 634, flow controller 638, controller 685, and enclosure 105 (e.g., a metal housing). Enclosure 105 houses gas lines 115 (e.g., input gas line 115-1 and input gas line 115-2), temperature sensor 697, heat source 175 (e.g., heat source 175-1 and heat source 175-2), and reaction chamber 628. Reaction chamber 628 includes porous medium 165.

In general, the porous medium 165 associated with gas generator system 100 enables quicker and more efficient generation of an oxidized mercury gas sample than conventional methods. For example, mercury source 650 (e.g., a gas cylinder of elemental mercury gas or a vapor generator, which utilizes the vapor pressure of liquid mercury to generate a known concentration of elemental mercury gas) feeds an elemental mercury gas to humidity controller 634.

Humidity controller 634 is configured to modify (e.g., increase or decrease) a relative humidity of the received elemental mercury gas provided by mercury source 650. In one embodiment, the humidity controller 634 controls the humidity level of the gas to be greater than 20% relative humidity, such as within a specified range of between 50% and 80%. For this relative humidity range, the corresponding temperature of gas sample at humidity controller 634 may be in the range of 15-35 degrees Celsius.

Humidifying (e.g., adding water vapor) to a mercury calibration gas sample enhances a flow of the gas sample (e.g., oxidized mercury) along a flow path. In other words, adjusting the relative humidity of the gas sample can help ensure that a majority of the elemental mercury and/or oxidized mercury in a gas sample does not stick to the walls of pipes, conduits, filters, etc. defining a flow path through gas line 115-1 and reaction chamber 628. According to one configuration, the humidity controller 634 includes a vessel of water that removes or adds water to the flowing gas sample (e.g., elemental mercury gas provided by mercury source 650) as it flows to gas line 115-1.

The output of the humidity controller 634 feeds into gas line 115-1. Gas line 115-1 (e.g., a metal pipe) feeds the elemental mercury gas into input 110 of reaction chamber 628. Thus, mercury source 650 provides a first type of gas input to reaction chamber 628.

Oxidizing agent source 640 provides a second type of gas input to reaction chamber 628. For example, oxidizing agent source 640 (e.g., a gas cylinder) provides an oxidizing agent gas such as chlorine gas. Flow controller 638 limits an amount of oxidizing agent gas (e.g., chlorine gas) that is fed through gas line 115-2 (e.g., a metal pipe) to input 110 of reaction chamber 628.

As mentioned, reaction chamber 628 includes porous medium 165 through which to pass a combination of the oxidizing agent gas and the elemental mercury gas received at the input 110. For example, the cross-sectional view of the reaction chamber 628 in FIG. 1 illustrates that the received gases must pass through porous medium 165 in order to pass to output 120. The surface area of pores in the porous medium 165 provide a site for heterogeneous surface reactions of the passing element mercury gas (e.g., input gas from mercury source 650) and the oxidizing agent gas (e.g., input gas from oxidizing agent source 640) to produce the outputted gas sample including oxidized mercury gas. In other words, the surface area of the porous medium 165 in reaction chamber 628 enhances a reaction between received chlorine gas and elemental mercury gas to produce the oxidized mercury gas.

As mentioned, passing of the elemental mercury gas and the oxidizing agent gas through the porous medium 165 supports a couple of functions. First, passing of received gases through the porous medium 165 enhances mixing of the elemental mercury gas with the oxidizing agent gas to enhance a reaction between the elemental mercury gas and the oxidizing agent gas (e.g., conversion of the elemental mercury gas into oxidized mercury gas). Second, use of the porous medium 165 increases an amount of surface area in a reaction chamber on which reactions (e.g., heterogeneous surface reactions) can take place between the elemental mercury gas and the oxidizing agent gas to form the oxidized mercury gas received at output 120.

As mentioned above, one hurdle associated with producing an oxidized mercury gas sample is the relatively difficult task of converting elemental mercury gas into an oxidized mercury gas. Mere mixing of elemental mercury gas and an oxidizing agent gas in a reaction chamber typically can produce a small amount of oxidized mercury gas according to conventional techniques. However, such a method does not typically yield a high enough quantity of oxidized mercury for calibrating a mercury monitoring system. Use of the porous medium 165 in reaction chamber 628 as described herein can easily increase a conversion rate from elemental mercury gas to oxidized mercury gas to greater than 80%, assuming enough oxidizing agent gas is present in the reaction chamber 628 along with the elemental mercury gas to carry out such a reaction. In other words, without the porous medium 165 in the reaction chamber 628 and based on the difficulty of producing oxidized mercury gas, there may be a reaction of about 10% of the elemental mercury gas into oxidized mercury gas. Use of an appropriate porous medium 165 in the reaction chamber 628 can enable conversion of more than 80% of the elemental mercury gas into oxidized mercury gas (assuming that there is an oxidizing agent gas present in the reaction chamber 628).

Additionally, passing of the received elemental mercury gas and the received oxidizing agent gas through the porous medium can account for 80% or more of the oxidized mercury gas that is produced by reaction chamber 628. In other words, 80% or more of the oxidized mercury can be created based on a mixing and reaction of elemental mercury gas and oxidizing agent gas in the porous medium 165.

Based on its corresponding characteristics such as presence of internal pores, the porous medium 165 is relatively compact in size (e.g., the porous medium 165 occupies a reasonable volume of space) but yet provides a relatively large surface area for carrying out a reaction between the received elemental mercury gas and the oxidizing agent gas. Accordingly, use of porous medium 165 in reaction chamber 628 can substantially increase an amount of surface area in reaction chamber 628 to carry out a reaction without substantially increasing a size of the chamber so that it is prohibitively large. Also, use of the porous medium 165 enables a fairly speedy reaction between the received elemental mercury gas and the oxidizing agent gas.

The porous medium 165 can be chosen from many different types of materials. For example, the porous medium 165 can be made from metal such as stainless steel, copper, etc. According to other embodiments, the porous medium 165 is made from a material such as ceramic, Hastelloy™, quartz, etc.

In one embodiment, surfaces of the pores in the porous medium 165 are coated with a protective material such as silica or glass. Providing a coating or thin layer of material on the pores of the porous medium 165 can protect the porous medium 165 from being damaged by the passing of elemental mercury gas, the oxidizing agent gas, and/or any other gases or fluids passed through the porous medium 165. One way to coat the pores of porous medium 165 is use of a deposition process.

Sizes of pores in the porous medium 165 can vary depending on the application. For example, according to one implementation, the porous medium 165 has a nominal pore size in a range between 0.1 micrometers and 500 micrometers. The pores (e.g., cavities) in the porous medium 165 can be of the same or substantially different sizes. According to other embodiments, the nominal pore size can be in a range between 0.1 and 20 microns as well as up to a range between 0.1 and 100 microns.

In an example embodiment, the porous medium 165 has a nominal pore size (e.g., a size of the sintered metal cavities in the porous medium 165) of 5 micrometers and is available as part number 1401612-01-050 manufactured by the Mott Corporation in Farmington, Conn. This is a sintered stainless steel tubing (e.g., Mott™ 1400 Series Sintered Porous Seamless Tube in 316LSS) having dimensions of 0.375" Outer Diameter×0.250" Inner Diameter×24.0" long, and a media grade 5 micrometer nominal pore size. The tube can be cut to a size in a range between 4 and 6 inches, although any length of porous medium 165 tube can be used in reaction chamber 628 to enhance a reaction.

As an alternative to the above part, the porous medium 165 in reaction chamber 628 also can be part number 6401510-050 manufactured by Mott as mentioned above. This part is a pre-made, 5 micrometer sparger.

Although these are very specific parts for use as porous medium 165, note that any other porous medium of suitable characteristics (e.g., size, shape, material, etc.) can be used in reaction chamber 628 to enhance a conversion of elemental mercury gas into oxidized mercury gas.

Permeability characteristics (e.g., measure of the ease with which the gas can move through the porous medium 165) associated with porous medium 165 can vary depending on the application. However, according to one embodiment, the porous medium enables a flow 1 to 15,000 cubic centimeters of gas per minute with a back pressure (e.g., upstream pressure increase) from 0 to 150 millimeters of Hg (e.g., between 0 and 2.9 pounds per square inch, or between 0 and 19.998 Kilopascals).

Utilizing a porous medium 165 in reaction chamber 628 that imparts a limited back pressure on received gases at input 110 can be useful in applications in which mercury source 650 is a gas generator that produces the element mercury gas from evaporation of liquid mercury. Such systems are typically not capable of operating properly when exposed to high amounts of backpressure. Accordingly, one embodiment herein includes utilizing a porous medium 165 in reaction chamber 628 that enables a flow of gas through reaction chamber 628, but that provides a backpressure at input 110 such as less than 4 pounds per square inch as mentioned above. In other words, according to one embodiment, the difference in pressure between the gas at input 110 and output 120 can be as much as 4 pounds per square inch.

Heat sources 175 can be a clam-shell structure that clamps to or surrounds reaction chamber 628. In one embodiment, the heat sources 175 heat the reaction chamber 628 to heat the received elemental mercury gas and the oxidizing agent gas in the reaction chamber 628 prior to passing of the elemental mercury gas and the oxidizing agent gas through the porous medium 165.

Gas generator system 100 includes a controller 685 that receives feedback from temperature sensor 697. Temperature sensor 697 produces a signal that corresponds to the temperature of air within enclosure 105.

The controller 685 controls an amount of heat produced by the heat sources 175 such that the temperature in the enclosure and/or temperature of received element mercury gas and the oxidizing agent gas are maintained at a temperature between 30 and 650 degrees Celsius or within a range such as between 40 and 450 degrees Celsius. Temperatures higher than 800 degrees Celsius tend to cause oxidized mercury gas to break down into elemental mercury gas while temperatures below 20 degrees Celsius do not sufficiently enhance reactions in the reaction chamber 628. Thus, embodiments herein include heating the enclosure 105 (and passing gas) to a temperature range between 200 and 450 degrees Celsius. In one embodiment, the controller 685 keeps the temperature in enclosure 105 at approximately 350 degrees Celsius.

Initially, the temperature of the gases from mercury source 650 and oxidizing agent source 640 may be around room temperature when emitted from respective sources 640 and 650. Heat from heat sources 175 heats the ambient air as well as gas lines 115 in enclosure 105. Since the gas lines 115 are heated, the gases passing through the gas lines 115 also becomes heated prior to entering input 110 of reaction chamber 628.

Accordingly, in one embodiment, the heat sources 175 are configured to heat the reaction chamber 165 as well as gases in the input gas line 115-1 and the input gas line 165-2 in the enclosure 105 (e.g., a metal housing substantially encasing the reaction chamber 628, the gas lines 115, and the temperature sensor 697) prior to entering the input 110 of the reaction chamber 628 and passing through porous medium 165. Preheating and heating of the gases in this way enhances a reaction of the gases to produce the oxidized mercury as well as reduces an amount of mercury/oxidized mercury that sticks to the walls of the gas lines 115, reaction chamber 628, porous medium 165, etc.

Providing heat sources 175 along a length of the reaction chamber 628 helps to ensure that an entire length of the porous medium 165 will be heated to an appropriate temperature to enhance chemical reactions therein. Otherwise, a presence of cold spots in the porous medium 165 may result in mercury/oxidized mercury sticking to pores of the porous medium 165 and/or poor conversion of elemental mercury gas into oxidized mercury gas.

Note again that use of the porous medium 165 in the reaction chamber 628 as discussed above need not always convert all of the elemental mercury gas into oxidized mercury. For example, in addition to emitting oxidized mercury gas, the reaction chamber can emit an unreacted portion of received oxidizing agent as well as an unreacted portion of received elemental mercury gas.

In certain test environments, as will be discussed later in this specification, it is desirable that the sample emitted from the chamber includes an approximate known ratio of oxidized mercury gas to unreacted elemental mercury gas (that was not converted in the reaction chamber 628).

Figure 2:
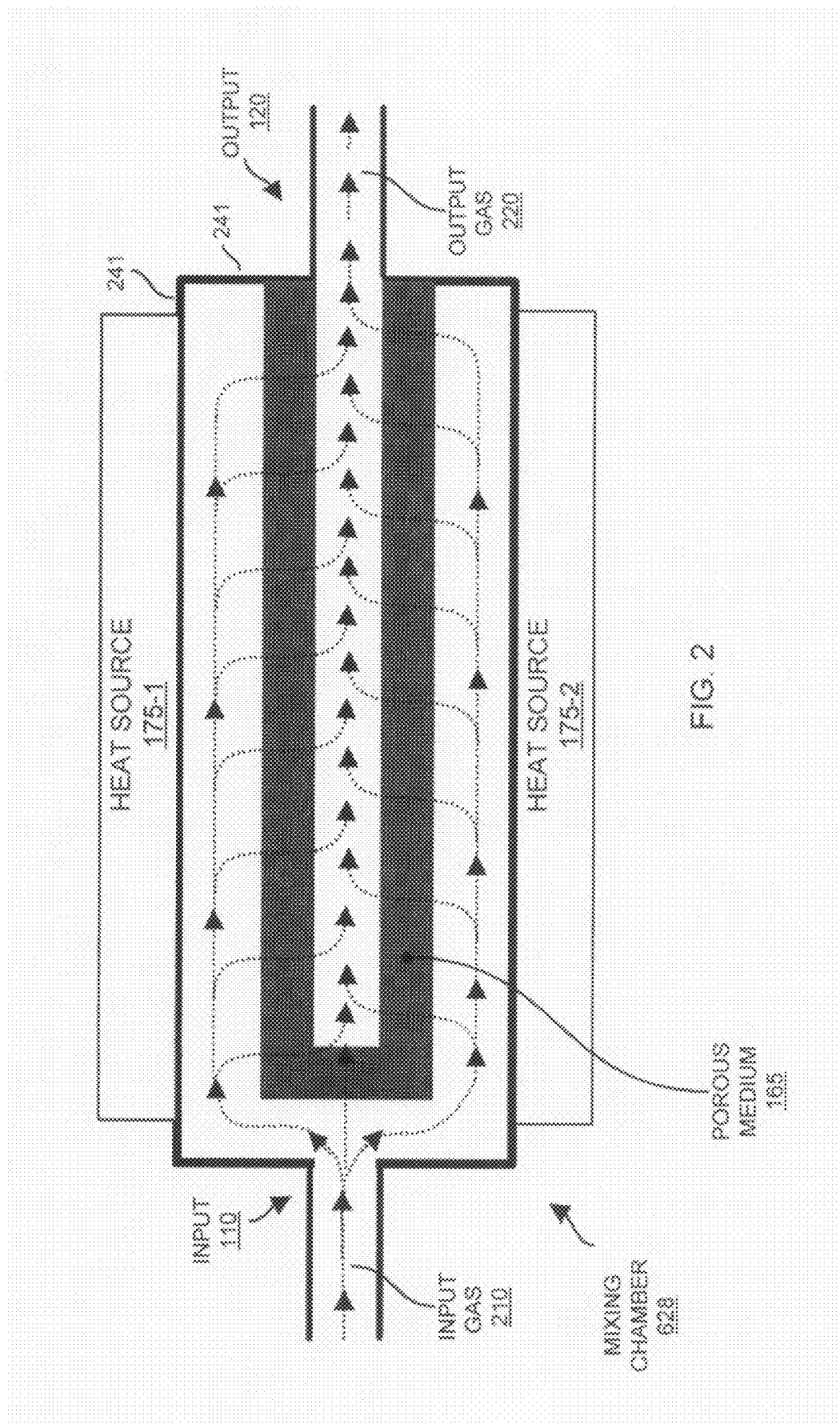
FIGS. 2-4 are diagrams illustrating different examples of reaction chambers according to embodiments herein.

FIG. 2 is a diagram illustrating reaction chamber 628 according to embodiments herein. In the context of this example, the outer portion (e.g., outer cylindrical walls in contact with heaters 175) of reaction chamber 628 is made from a length of cylindrical tube (e.g., a steel tube) configured to receive the input gas 210. The porous medium 165 can be a section of cylindrical tube of sintered stainless steel (cutaway side view shown) with a cap (at the leftmost end as shown) so that the received input gas 210 must pass through the porous medium 165 (so that the porous medium 165 is heated) in order to be emitted as output gas 220 at output 120. Thus, reaction chamber 628 can be configured to include an outer cylindrical wall (e.g., section of tube) as well as an inserted piece of inner cylindrical section of porous medium 165.

In such an embodiment, reaction chamber 628 receives input gas 210 (e.g., a combination of oxidizing agent gas and elemental mercury gas) at input 110. Reaction chamber 628 passes input gas 210 (e.g., the received elemental mercury gas and the received oxidizing agent gas) on illustrated paths through an outer surface of the cylindrical porous medium 165 to a core of the cylindrical porous medium 165 to the output 120 of the reaction chamber 628. This configuration enables generation of oxidized mercury gas using a relatively small sized reaction chamber 628.

As mentioned, heat sources 175 (e.g., heaters) supply heat to the reaction chamber 628. One purpose of directly heating the reaction chamber 628 (e.g., via contact of the heat sources with the outer walls of reaction chamber 628) is to heat the input gases 210 prior to passing through the porous medium 165.

Another purpose of heat sources 175 is to heat and enhance a reaction of the oxidizing agent gas and elemental mercury gas in the porous medium 165. For example, outer walls of reaction chamber 628 can be made from metal (or other heat conducting material) to provide a path from heat sources 175 through thermal paths 241 (e.g., walls of the reaction chamber 628) to porous medium 165. Thus, the reaction chamber 628 can be configured to provide a thermally conductive path from the heater sources 175 through the chamber to the porous medium 165 to enhance chemical reactions in the porous medium 165.

Figure 3:
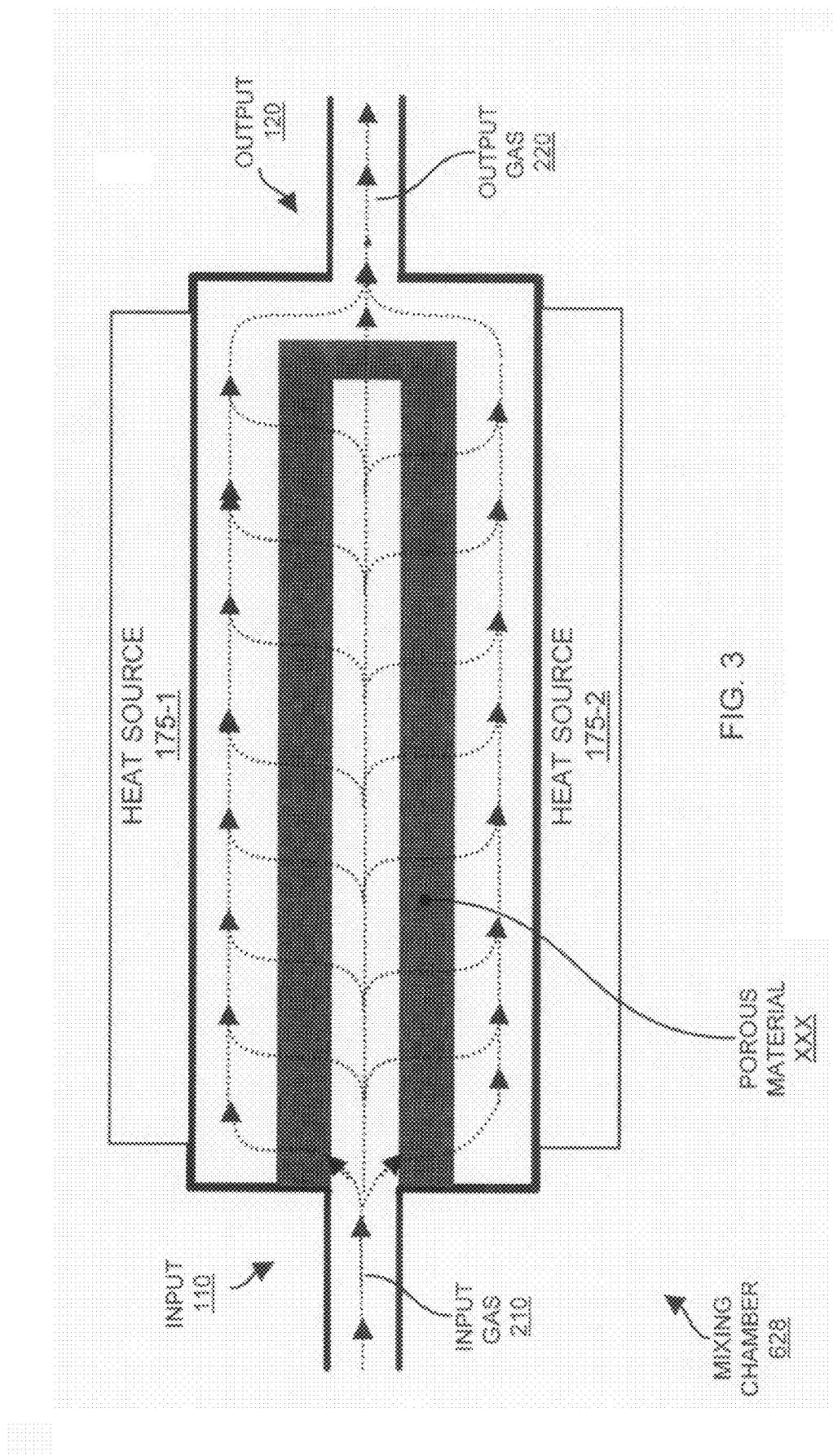

FIG. 3 is a diagram of reaction chamber 628 according to embodiments herein. As shown, the reaction chamber 628 includes a porous medium 165. In the context of the present example, the reaction chamber 628 is configured to pass received elemental mercury gas and the oxidizing agent gas (at input 110) on a path through an inner surface of the cylindrical porous medium 165 to an outer surface of the porous medium 165 to the output 120 of the reaction chamber 628. Such a configuration enhances reactions in the reaction chamber 628 in a similar as previously discussed.

Figure 4:
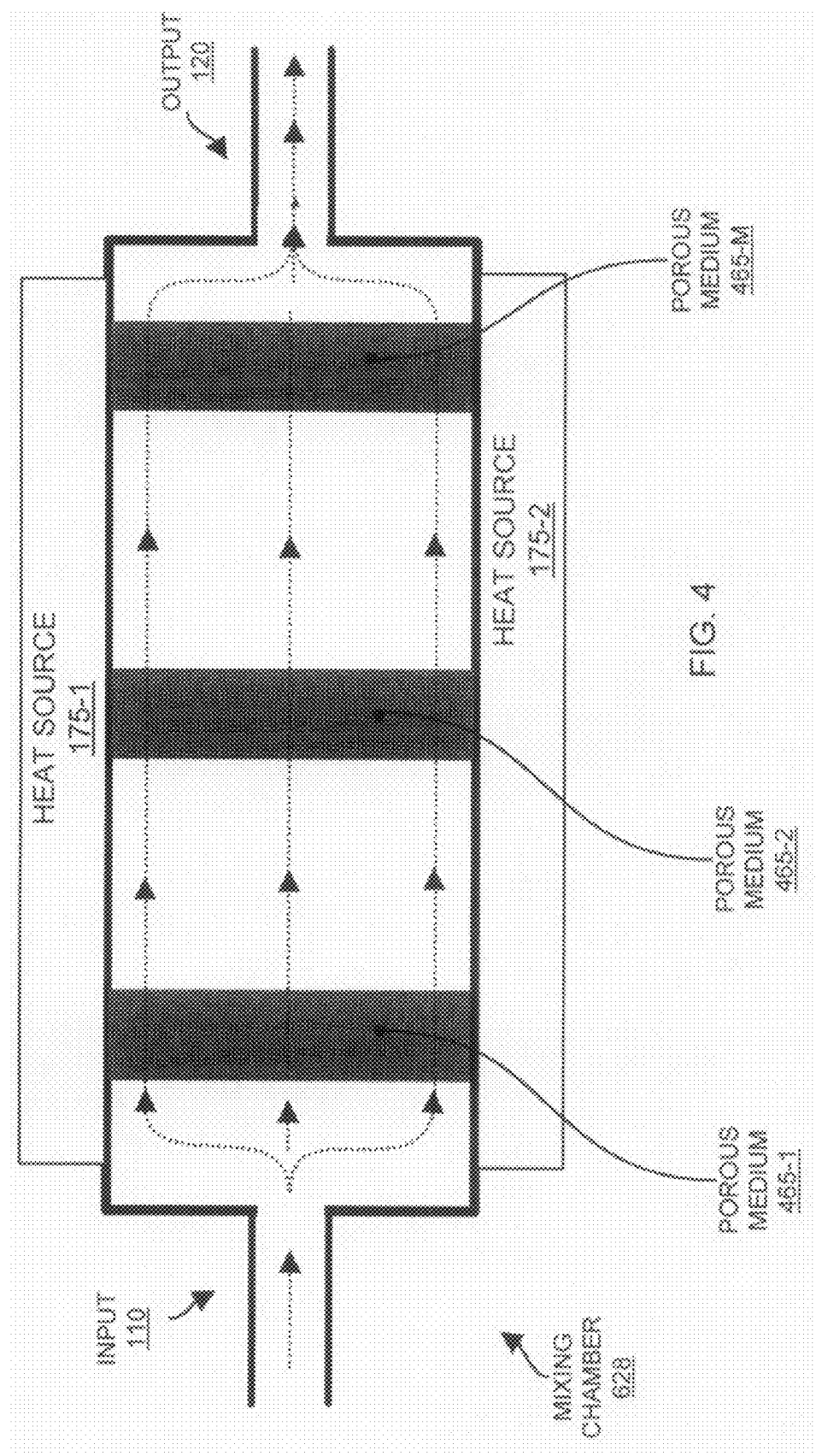

FIG. 4 is a diagram of yet another configuration of reaction chamber 628 according to embodiments herein. As shown, instead of a porous medium 165 made from a cylindrical tube as in FIGS. 1-3, the reaction chamber 628 in FIG. 4 includes one or more porous media 465 (e.g., porous medium 465-1, porous medium 465-2, . . . , porous medium 465-M). In the context of the present example, the porous media 465 includes one or more disk-shaped media that are disposed in reaction chamber 628 such that the elemental mercury gas and oxidizing agent gas received at input 110 must pass through the one or more porous media 465 for eventual emission at output 120. The porous media 465 enhances chemical reactions in a similar way as discussed above.

Figure 5:
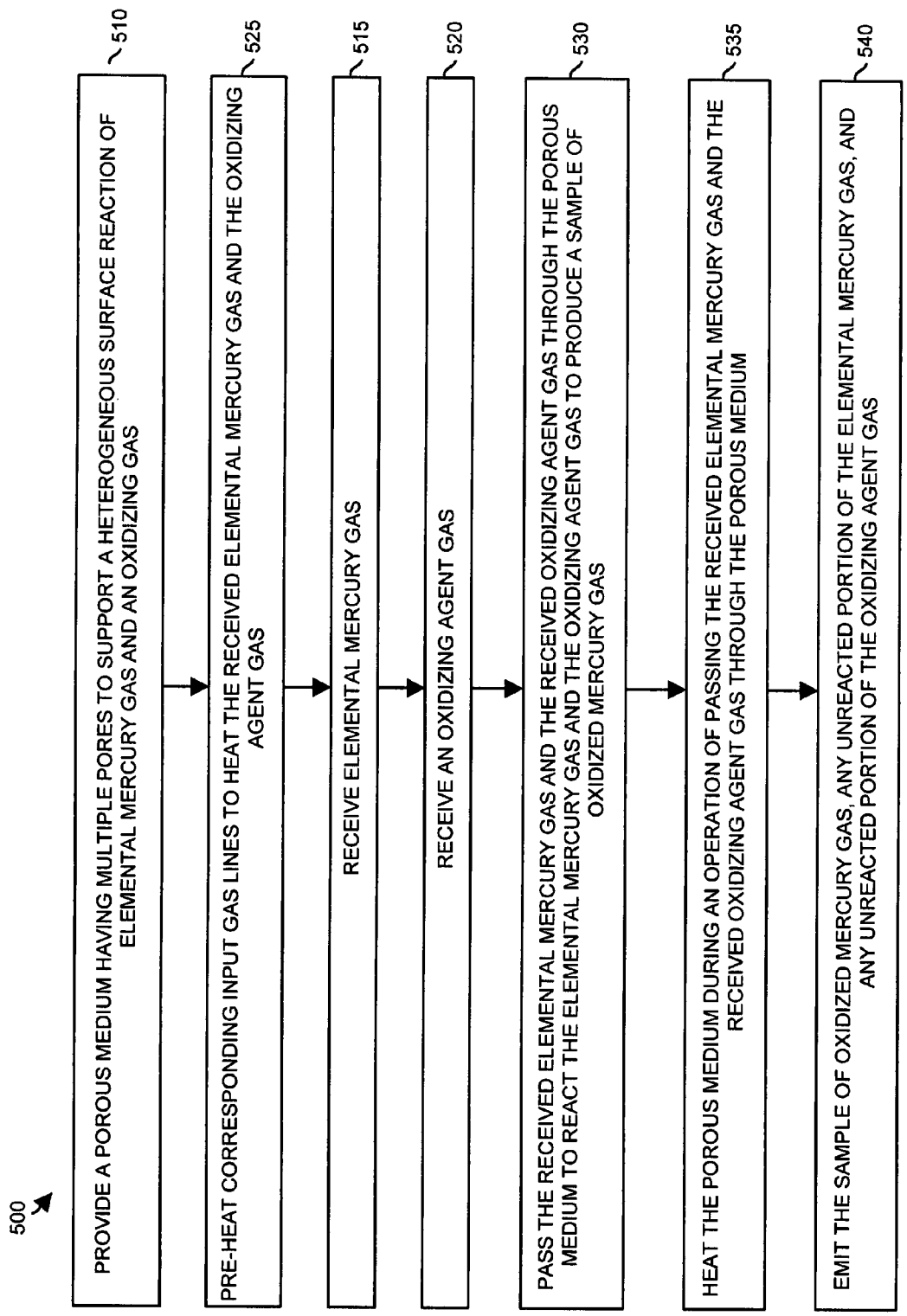
FIG. 5 is a diagram of a flowchart illustrating a method of producing an oxidized mercury gas sample according to embodiments herein.

FIG. 5 is a diagram of flowchart 500 illustrating a technique of producing oxidized mercury gas according to embodiments herein. Note that the steps in flowchart 500 summarize at least some of the techniques as discussed above.

In step 510, a manufacturer of the gas generator system 100 provides a porous medium 165 having multiple pores to support a heterogeneous surface reaction of elemental mercury gas and an oxidizing gas in reaction chamber 628.

In step 515, the controller 685 and heat sources 175 preheat corresponding input gas lines 115 and reaction chamber 628 via heating of ambient air in enclosure 105 and/or direct heating of reaction chamber 628 with heat sources 175.

In step 520, the reaction chamber 628 receives elemental mercury gas from input gas line 115-1.

In step 525, the reaction chamber 628 receives an oxidizing agent gas from input gas line 115-2.

In step 530, the reaction chamber 628 passes the received elemental mercury gas and the received oxidizing agent gas at input 110 through the porous medium 165 to react the elemental mercury gas and the oxidizing agent gas to produce a sample of oxidized mercury gas at output 120.

In step 535, the reaction chamber 628 heats the porous medium during an operation of passing the received elemental mercury gas and the received oxidizing agent gas through the porous medium 165.

In step 540, the reaction chamber 628 emits the sample of produced oxidized mercury gas for calibrating a mercury monitoring system.

Figure 6:
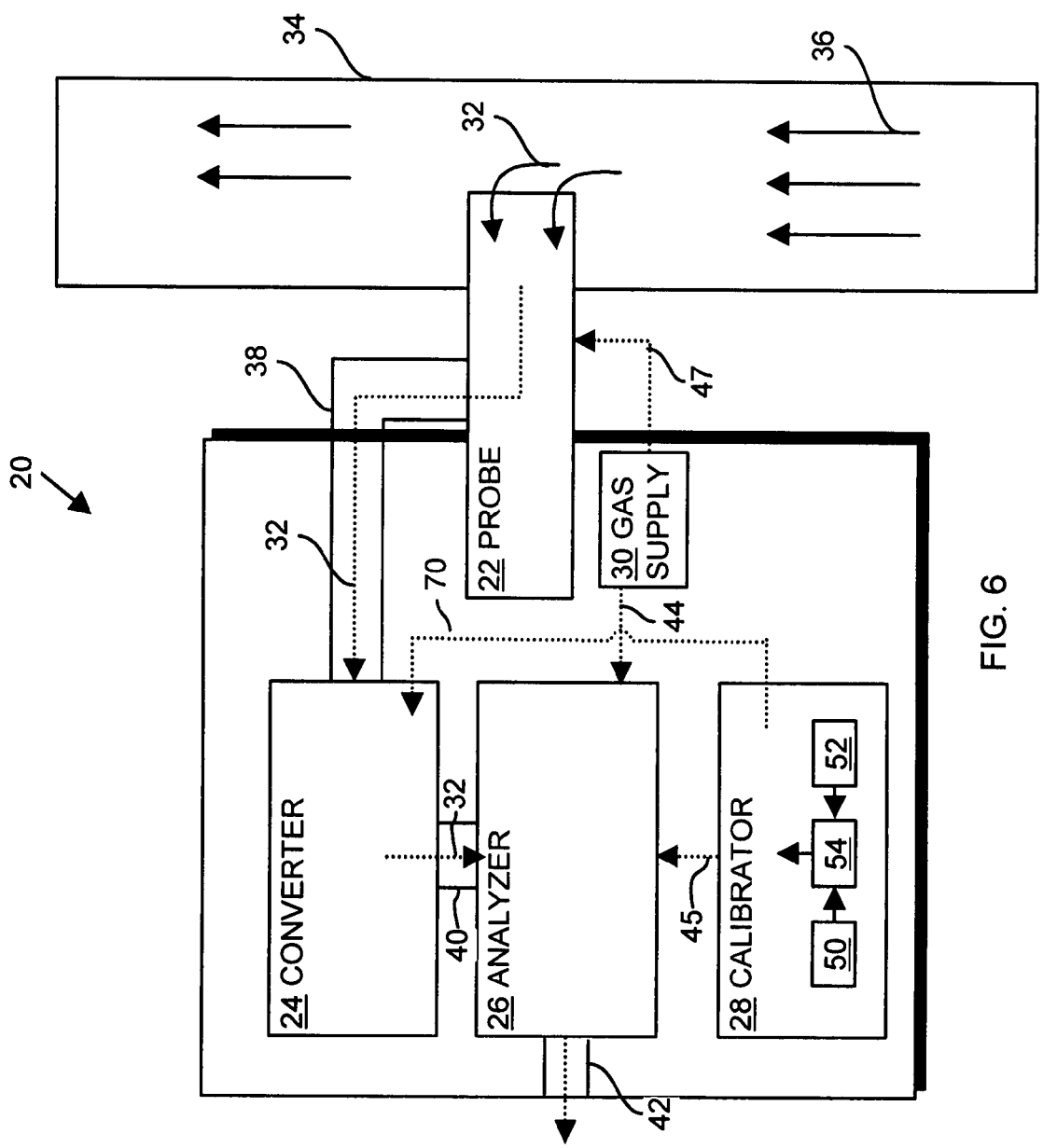
FIG. 6 is a schematic of a mercury monitoring system according to embodiments herein.

FIG. 6 illustrates a mercury monitoring system 20 for monitoring total mercury within a fluid sample, such as in an effluent gas from a coal-fired power plant, in a substantially continuous manner. The mercury monitoring system 20, or Continuous Emission Monitoring System (CEMS), includes a probe 22, a converter 24, an analyzer 26, a calibrator 28, and a dilution gas supply 30.

The probe (e.g., extraction probe) 22 is configured to receive a gas sample 32 from a sample source and deliver the gas sample 32 to the converter 24. For example, the probe 22 extends into, or is mounted proximate to, a stack or flue 34 of a coal combustion facility and collects, as the gas sample 32, a portion of the fluid or gas (e.g., effluent or emission) 36 flowing through the stack 34. The probe 22, in one arrangement, includes an inertial filter that separates particulate matter (e.g., flue ash) from the gas sample 32. Surfaces of the probe 22 that contact the gas sample 32 typically have a coating (e.g., silica or glass) that minimizes or prevents chemical reactions between the probe 22 and mercury present within the gas sample 32.

The probe 22 is connected to the converter 24 by way of a heated conduit 38 maintained at a temperature of, for example, 200° C. The heated conduit 38 limits condensation of the gas sample 32 and "sticking" of vaporized mercury to the conduit 38 and provides efficient transport of the gas sample 32 to the converter.

The converter 24 receives the gas sample 32 from the probe 22 and is operable to convert the vapor-phase species of mercury (e.g., oxidized mercury) present within the gas sample 32 into elemental mercury and to maintain the mercury in the elemental form so as to allow the analyzer 26 to detect the total mount of mercury present within a gas sample. For example, in one arrangement, the converter 24 converts oxidized forms of mercury, $Hg^{+2}$ (e.g., $HgCl_2$, $Hg(NO_3)_2$) into elemental mercury, $Hg^0$, by applying a relatively high temperature to the gas sample 32.

The analyzer 26 is connected to the converter 24 by way of a heated conduit 40 and receives the heated gas sample 32 from the converter 24. In one arrangement, the analyzer 26 is an atomic fluorescence analyzer that measures or detects an amount or a concentration of elemental mercury present within the gas sample 32. Upon completion of the detection process, the analyzer 26 exhausts the gas sample 32 to the atmosphere via an exhaust port 42.

Typically, the analyzer 26 requires periodic calibration in order to accurately detect or measure the presence of elemental mercury within a gas sample 32. Calibration is provided by the calibrator 28 which, in one arrangement is in fluid communication with the analyzer 26 through a line or conduit 45 and provides vaporized elemental mercury to the analyzer 26 at a particular concentration, such as by using a Peltier cooler/vapor pressure control and mass flow controllers. The analyzer 26 compares the amount of elemental mercury received from the calibrator 28 with that of dry, substantially mercury-free gas, received from the dilution gas supply 30 via conduit 44. The results of such a comparison allow direct calibration of the analyzer 26.

In certain cases, the analyzer 26 requires periodic calibration in order to accurately detect or measure the presence of both elemental and oxidized mercury within a gas sample 32.

The calibrator 28 is connected to the converter 24 and provides a known concentration of oxidized mercury, such as in the form of a mercury-containing vapor, to the converter 24. By providing oxidized mercury having a known concentration, the calibrator 28 allows calibration of the analyzer 26 within the mercury monitoring system 20.

Figure 7:
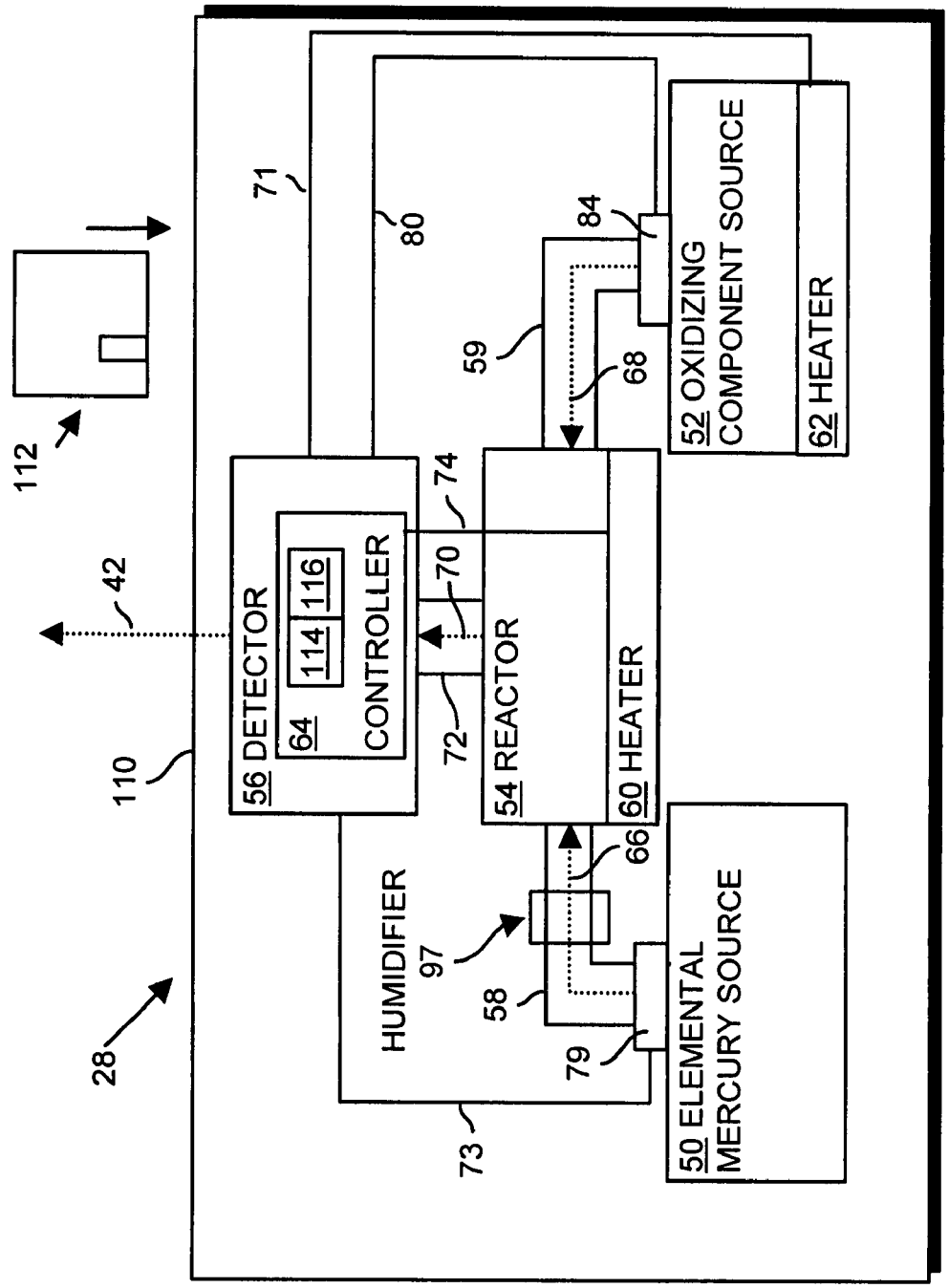
FIG. 7 illustrates an arrangement of a mercury system calibrator as used within the mercury monitoring system of FIG. 1 according to embodiments herein.

FIG. 7 illustrates an arrangement of the calibrator 28. The calibrator 28 includes an elemental mercury source 50, an oxidizing component source 52, and a reactor 54 (e.g., a reaction chamber 628 as discussed above) coupled to the elemental mercury source 50 and the oxidizing component source 52.

The elemental mercury source 50 is connected to the reactor by a conduit 58 and provides a stream of elemental mercury 66, having a known concentration, to the reactor 54. For example, in one arrangement, the elemental mercury source 50 includes a vapor generator with liquid elemental mercury that evaporates into elemental mercury in response to application of a particular pressure and temperature. In such an arrangement, the vapor generator (e.g., elemental mercury source 50) enables a flow of gas or air (e.g., substantially mercury-free gas) through the evaporated elemental mercury and delivers the vaporized mercury to the reactor 54 as a vapor stream having a known (e.g., operator determined) concentration of vaporized mercury within the vapor stream.

In another arrangement, the elemental mercury source 50 includes a permeation device. The permeation device contains elemental mercury in a two-phase state (liquid and gas). At a substantially constant temperature, the permeation device emits gaseous elemental mercury at a substantially constant rate through a permeable element (e.g., Teflon housing) and the elemental mercury gas 66 is delivered to the reactor 54 via the conduit 58.

The calibrator 28 can include a humidifier device 97 through which the elemental mercury gas 66 passes prior to being delivered to reactor 54. In one embodiment, the humidifier device 97 includes a Model MH-110-48F-4 Nafion dryer manufactured by Perma Pure, LLC, Toms River, N.J. Such a device can include a vessel filled with liquid water that produces water vapor that is added to the mercury gas 66 passing through conduit 58. Thus, humidifier device 97 can add (or potentially remove) water vapor to change (e.g., increase or decrease) a relative humidity level of the elemental mercury gas 66 in conduit 58. In one configuration, the humidifier device 97 generates a relative humidity level of the elemental mercury gas 66 of greater than 20%, such as in a range between 50% and 80%. The temperature in or around a vicinity of the humidifier device 97 and corresponding conduit 58 may be in the range of about 15 to 45 degrees Celsius. However, note that an amount of water vapor added to the mercury gas 66 passing through conduit 58 can be adjusted within different relative humidity ranges for different temperatures so that the elemental mercury gas 66 does not condense downstream.

One purpose of humidifying (e.g., increasing an amount of water vapor in the) elemental mercury gas 66 via humidifier device 97 is to reduce a "stickiness" associated with the gaseous mercury (e.g., elemental mercury gas 66, mercury halide in output 70, etc.). For example, increasing a concentration of water vapor reduces the likelihood that gaseous mercury 66 will stick to the walls of conduit 58, reactor 54, conduit 72, etc. as the gaseous mercury progresses towards detector 56. Reducing an amount of mercury deposited on the walls of conduit 58, reactor 54, etc. ensures that such deposits do not (or minimally) interfere with future reactions of producing output stream 70.

The oxidizing component source 52 is connected to the reactor 54 by a conduit 59 and provides a mercury oxidizing component 68 to the reactor 54. For example, the oxidizing component source 52 provides chlorine (e.g., $Cl_2$) to the reactor 54 to oxidize the elemental mercury 66 received by the reactor 54. In one arrangement, the oxidizing component source 52 is configured as a container holding a chlorine generating chemical that, upon heating, generates chlorine in a gaseous phase.

In one arrangement, the oxidizing component source 52 includes a heater 62 and a mercury oxidizing component 68 such as palladium chloride (e.g., $PdCl_2$) or tungsten chloride in solid form. In such cases, the heater 62 increases the temperature of the palladium chloride within the oxidizing component source 52 to cause thermal separation of the palladium component from the chlorine component. The separated chlorine is then directed from the oxidizing component source 52 to the reactor 54 as chlorine gas 68. In another arrangement, the oxidizing component may be delivered from a gas cylinder.

In yet another arrangement, the oxidizing component source can be a nitrate source such as lead nitrate. Thermal separation of nitrate occurs when exposing the lead nitrate to a sufficient temperature.

The reactor 54 is configured to receive elemental mercury 66 from the elemental mercury source 50 and the mercury oxidizing component (e.g., chlorine) 68 from the oxidizing component source 52 and combine the oxidizing component 68 with the elemental mercury 66 to form an output or output stream 70 that includes elemental mercury gas (assuming that not all of the mercury from elemental mercury source 50 is oxidized) and mercury chloride ($HgCl_2$) gas. The reactor 54, in one arrangement, defines a chamber for mixing of the elemental mercury gas 66 and the chlorine gas 68 and includes a heater 60, such as a heating coil in thermal communication with the chamber. The heater 60 delivers thermal energy (e.g., heat) to the chamber to promote combining of the elemental mercury gas 66 and the chlorine gas 68 to form mercury chloride ($HgCl_2$).

As indicated above, the calibrator 28 generates known concentrations of oxidized mercury for calibrating continuous emission monitoring systems requiring accurate responses to both elemental mercury and oxidized mercury. The following describes an example of operation of the calibrator 28.

Figure 8:
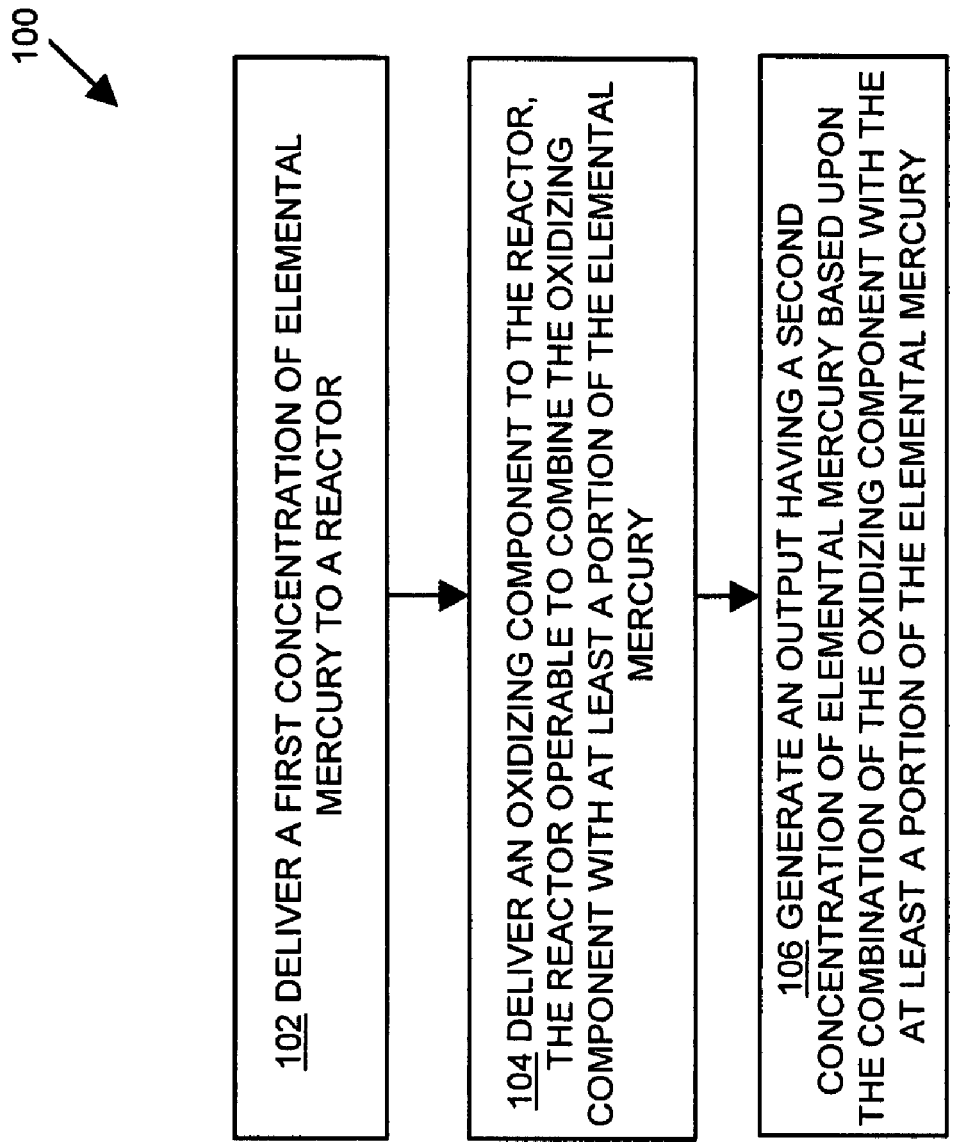
FIG. 8 is a flow chart of a procedure performed by the mercury system calibrator of FIG. 2 according to embodiments herein.
Figure 9:
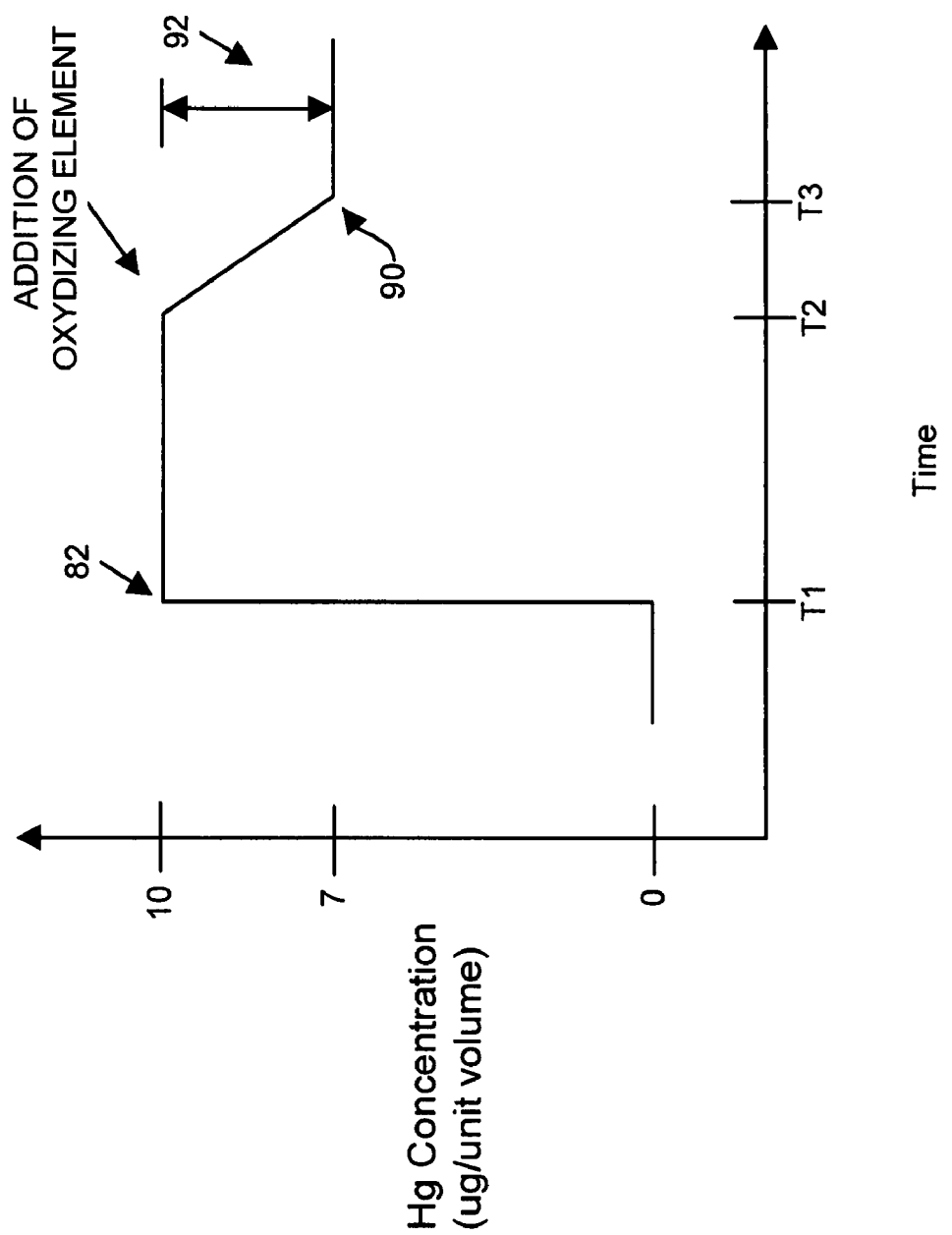
FIG. 9 is a graph illustrating detection of oxidized mercury generated by the mercury system calibrator according to embodiments herein.

FIG. 8 is a flow chart 100 of a procedure performed by the calibrator 28 to generate a known concentration of oxidized mercury for calibration of a mercury monitoring system 20. FIG. 9, taken in conjunction with FIG. 8, illustrates a concentration of elemental mercury within the output 70 during the procedure (e.g., before and after addition of the mercury oxidizing component 68 to the elemental mercury gas 66 held by the reactor 54).

In step 102, in the calibrator 28, the elemental mercury source 50 delivers a first concentration of elemental mercury 66 to a reactor 54. For example, the elemental mercury source 50 of the calibrator 28 generates an elemental mercury stream 66 having a known or first elemental mercury concentration value, $[Hg^0]_1$. As illustrated in FIG. 4, at a first time T1, the elemental mercury stream 66 (which is flowing from the elemental mercury source 50 via the conduit 58 to the reactor 54) may have a first, known concentration value 82 of 10 micrograms/unit volume.

Returning to FIG. 8, in step 104, the oxidizing component source 52 in the calibrator 28 delivers an oxidizing component 68 to the reactor 54, which may be operated at approximately room temperature (e.g., 22° C.) or an elevated temperature such as between 200 and 500 degrees Celsius. The reactor 54 combines the oxidizing component 68 with the elemental mercury 66. For example, as illustrated in FIG. 4, at a second time T2, the oxidizing component source 52 provides chlorine gas (e.g., $Cl_2$) 68 to the reactor 54 as a fluid flow, carried by the conduit 59, to oxidize the elemental mercury 66 received by the reactor 54. As indicated above, the reactor 54 defines a chamber that allows for mixing of the elemental mercury (e.g., gas) 66 and the chlorine gas 68 to form mercury chloride ($HgCl_2$) gas. In one arrangement, the reactor receives a thermal input (e.g., heat) from the heater 60 to promote rapid combining of the chlorine gas 68 with the elemental mercury 66 to form mercury chloride ($HgCl_2$) gas.

Returning to FIG. 8, in step 106 the calibrator 28 generates an output 70 having a second concentration of elemental mercury (e.g., at least a portion of the elemental mercury) based upon the combination of the oxidizing component 68 with the elemental mercury 66. Since the chlorine gas 68 combines with a portion (e.g., a percentage) of the elemental mercury 66 present within the reactor to form mercury oxide gas, as illustrated in FIG. 9 in the interval between the second time T2 and a third time T3, the concentration of elemental mercury within the reactor 54 decreases from the concentration delivered to the reactor 54 from the elemental mercury source 50. For example, the concentration of elemental mercury decreases from a first concentration 82 of 10 micrograms/unit volume to a second concentration 90 of 7 micrograms/unit volume. The calibrator 28 releases the output 70 (e.g., output stream) having the second concentration 90.

Returning to FIG. 7, in one arrangement, the calibrator 28 includes a detector 56. The detector 56 is connected to the reactor 54 via a conduit 72 and is configured to receive the output stream 70 from the reactor 54. The detector 56 includes a controller 64, such as a processor 114 and a memory 116. The detector 56, such as an atomic fluorescence spectrometer, in conjunction with the controller 64, is configured to detect a concentration of elemental mercury within the output 70. For example, the detector 56 utilizes atomic fluorescence spectroscopy to measure the concentration of elemental mercury present within the reactor output 70. The detector 56 (e.g., the controller 64 of the detector 56) also compares the concentration of elemental mercury 66, $[Hg^0]_2$ (e.g., the second concentration 90 of elemental mercury) present within the reactor output 70 with the known concentration of elemental mercury 66 produced by the elemental mercury source 50. The detected difference in elemental concentrations allows for the calculation of a concentration of oxidized mercury within the output 70, as described below.

For example, the detector 56 calculates a difference between the first concentration 82 of elemental mercury and the second concentration 90 of elemental mercury within the output 70 to detect a concentration of oxidized mercury within the output 70. For example, the controller 64 receives a second concentration value of the elemental mercury within the output 70 from the detector 56. The controller 64 subtracts the second, reduced elemental mercury concentration $[Hg^0]_2$ from the first, known elemental mercury concentration $[Hg^0]_1$. The difference between $[Hg^0]_1$ and $[Hg^0]_2$, illustrated in FIG. 9 as a change 92 in the elemental mercury concentration, is substantially equal to the concentration of oxidized mercury (e.g., $HgCl_2$) produced by the calibrator 28. By providing oxidized mercury at a measurable concentration, the calibrator 28 allows a user to calibrate continuous emission monitoring systems 20 for accurate response to both elemental mercury and oxidized mercury.

Returning to FIG. 7, in one arrangement, the controller 64 controls the thermal output of the heater 60 of the reactor 54 through an electrical line 74. The controller 64 activates the heater 60 associated with the reactor 54 to provide heat to the elemental mercury 66 and oxidizing component 68 within the reactor 54, promoting the formation of oxidized mercury. The controller 64 may also adjust the thermal output of (e.g., level of heat provided by) the heater 60 to adjust the rate of combination of the elemental mercury 66 and oxidizing component 68 and thus the concentration of oxidized mercury present within the output 70.

During operation, the controller 64 calculates the concentration of oxidized mercury within the output 70. In the case, for example, where a particular application requires the calibrator 28 to produce oxidized mercury at a particular preset concentration, the controller 64 compares a preset oxidized mercury concentration value (e.g., threshold value) with a calculated oxidized mercury value. If the preset oxidized mercury concentration value is not equal to the calculated oxidized mercury value, the controller 64 adjusts the thermal output of the heater 60 to either raise or lower the temperature of the reactor 54 (e.g., raise or lower the temperature of the elemental mercury 66 and the oxidizing component 68 within the reactor 54) so as to vary the extent of reaction of elemental mercury 66 and the oxidizing component 68, thereby adjusting the concentration of mercury oxide present within the output 70.

In one arrangement, the controller 64 is electrically connected to, and controls, the heater 62 associated with the oxidizing component source 52 through an electrical line 71. As indicated above, in one arrangement, the oxidizing component 68 contained by the oxidizing component source 52 is an oxidized metal, such as palladium chloride (i.e., $PdCl_2$) or tungsten chloride. During operation, the controller 64 activates the heater 62 to provide heat (e.g., the heater operates at a temperature of approximately 300° C.) to the oxidized metal, liberating chlorine gas, which flows from the oxidizing component source 52 to the reactor 54.

The controller 64, in one arrangement, is also configured to adjust a thermal output of (e.g., a level of heat provided by) the heater 62 to adjust the rate of separation of the oxidized metal into a metal component and an oxidizing component 68. By adjusting the rate of separation, the controller 64 can adjust the amount of the oxidizing component 68 delivered by the oxidizing component source 52 to the reactor 54 and thereby adjust the concentration of oxidized mercury present within the output 70.

During operation, the controller 64 calculates the concentration of oxidized mercury within the output 70. In the case, for example, where a particular application requires the calibrator 28 to produce oxidized mercury at a particular preset concentration, the controller 64 compares a preset oxidized mercury concentration value (e.g., threshold value) with a calculated oxidized mercury value. If the preset oxidized mercury concentration value is not equal to the calculated oxidized mercury value, the controller 64 adjusts the thermal output of the heater 62 to either increase or decrease the rate of separation of the oxidized metal into a metal component and an oxidizing component 68. By changing the rate of separation of the oxidized metal, the controller 64 increases or decreases the amount of the oxidizing component 68 (e.g., chlorine gas) available within the reactor 54 to chemically combine with the elemental mercury 66 within the reactor 54. As a result, the controller 64 adjusts the concentration of mercury oxide created within the reactor 54 and provided within the output 70 from the reactor 54.

In one arrangement, the controller 64 adjusts the amount of the elemental mercury 66 provided to the reactor 54 by the elemental mercury source 50 during operation. For example, in one arrangement, the controller 64 is electrically connected through an electrical line 73 to a valve 79 associated with the elemental mercury source 50 and in flow communication with the conduit 58. By increasing or decreasing the flow volume of elemental mercury 66 to the reactor 54, the controller 64 adjusts the amount of elemental mercury 66 within the reactor 54 available to chemically combine with the oxidizing component present. As a result, by adjusting the amount of the elemental mercury 66 provided to the reactor 54, the controller 64 adjusts the concentration of mercury oxide created within the reactor 54 and provided within the output 70 from the reactor 54.

For example, during operation, the controller 64 calculates the concentration of oxidized mercury within the output 70. The controller 64 compares a preset oxidized mercury concentration value (e.g., a threshold value) with the calculated oxidized mercury value. If the preset oxidized mercury concentration value is not equal to the calculated oxidized mercury value, the controller 64 adjusts (e.g., increases or decreases) the amount of the elemental mercury 66 delivered to the reactor 54, such as by adjusting the valve of the elemental mercury source 50. By adjusting the amount of the elemental mercury 66 provided to the reactor 54, the controller 64 adjusts the concentration of mercury oxide created within the reactor 54 and provided within the output 70 from the reactor 54.

In one arrangement, the controller 64 adjusts the amount of the oxidizing component 68 provided to the reactor 54 by the oxidizing component source 52 during operation. For example, in one arrangement, the controller 64 is electrically connected through an electrical line 80 to a valve 84 associated with the oxidizing component source 52 and in flow communication with the conduit 59. By increasing or decreasing the flow volume of the oxidizing component 68 to the reactor 54, the controller 64 adjusts the amount of the oxidizing component 68 within the reactor 54 available to chemically combine with the elemental mercury 66 present. As a result, by adjusting the amount of the oxidizing component 68 provided to the reactor 54, the controller 64 adjusts the concentration of mercury oxide created within the reactor 54 and provided within the output 70 from the reactor 54.

For example, during operation, the controller 64 calculates the concentration of oxidized mercury within the output 70. The controller 64 compares a preset oxidized mercury concentration value (e.g., a threshold value) with the calculated oxidized mercury value. If the preset oxidized mercury concentration value is not equal to the calculated oxidized mercury value, the controller 64 adjusts (e.g., increases or decreases) the amount of the oxidizing component 68 delivered to the reactor 54, such as by adjusting the valve of the elemental mercury source 50. By adjusting the amount of the oxidizing component 68 provided to the reactor 54, the controller 64 adjusts the concentration of mercury oxide created within the reactor 54 and provided within the output 70 from the reactor 54.

Figure 10:
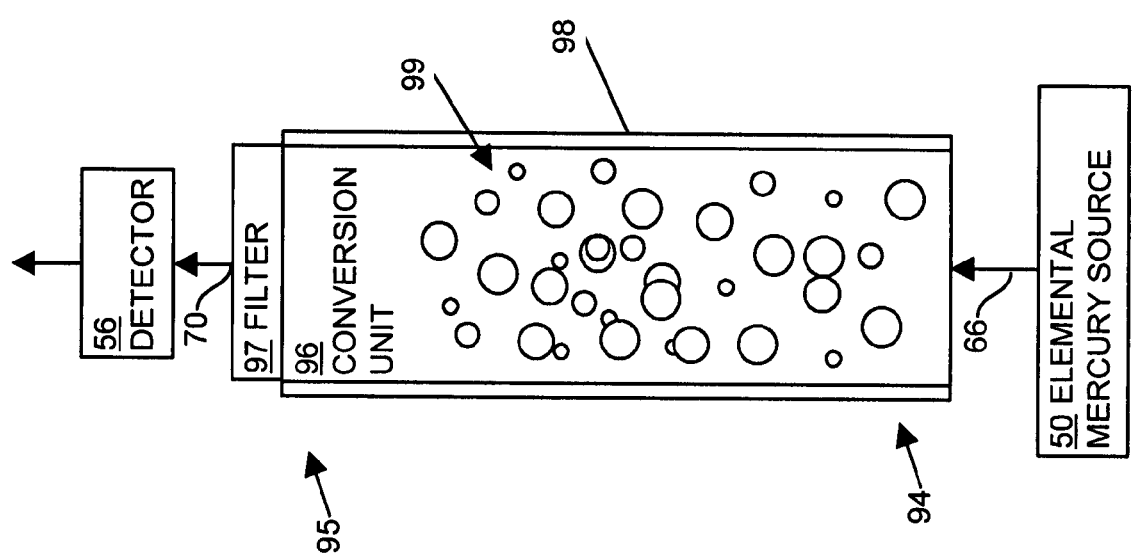
FIG. 10 illustrates an arrangement of a mercury system calibrator as used within the mercury monitoring system of FIG. 1 according to embodiments herein.

FIG. 10 illustrates an arrangement of the calibrator 28 where the reactor 54 and the oxidizing component source 52 form a single, integrated conversion unit 96. Such an arrangement minimizes the number of components required by the calibrator 28 to generate a known concentration of mercury oxide.

The conversion unit 96 has a first end 94 and a second end 95. The first end 94 is connected to the elemental mercury source 50 and is operable to direct elemental mercury 66 through the conversion unit 96 toward the second end 95. The second end 95 is connected to the detector 56 and is operable to direct an output 70 (e.g., a combination of elemental mercury and oxidized mercury in gaseous phase) toward the detector 56. The conversion unit 96 includes a filter 97 and a heater 98 and contains an oxidized metal 99, such as palladium chloride (i.e., $PdCl_2$).

The heater 98 is operable to heat materials within the conversion unit 96 and serves a dual purpose. First, the heater 98 is configured to increase the temperature of oxidized metal 99 within the conversion unit 96 to cause thermal separation of the metal component from the oxidizing component. Second, the heater 98 is configured to deliver thermal energy or heat to the conversion unit 96 to increase the temperature of the elemental mercury gas 66 and the oxidizing component (e.g., chlorine gas) 68 present within the conversion unit 96. Such an increase in temperature promotes combination of the elemental mercury gas 66 and the chlorine gas 68 to form mercury chloride ($HgCl_2$).

Returning to FIG. 7, the calibrator 28, in one arrangement, is configured as a computerized device 110. A computer program product 112 includes an application or logic instructions that are loaded into the computerized device 110 to configure the device 110 to perform as a calibrator 28.

The computerized device 110 includes the controller 64 that, in one arrangement, includes a memory 114 and a processor 116. The memory 114 can be of any type of volatile or non-volatile memory or storage system such as a computer memory (e.g., random access memory (RAM), read only memory (ROM), or another type of memory) disk memory, such as hard disk, floppy disk, optical disk, for example. The memory 114 is encoded with logic instructions and/or data that, in one embodiment of the computerized device 110, form a calibrator application configured according to embodiments of the calibrator 28. In other words, the calibrator application represents software coding instructions and/or data that reside within the memory or storage 114, or within any computer readable medium accessible to the computer device 110.

The processor 116 may be any type of circuitry or processing device such as a central processing unit, controller, application specific integrated circuit, programmable gate array, or other circuitry that can access the calibrator application encoded within the memory 114 in order to run, execute, interpret, operate, or otherwise perform the calibrator application logic instructions. In other words, in another embodiment of the computer device 110, a calibrator process represents one or more portions of the logic instructions of the calibrator application while being executed or otherwise performed on, by, or in the processor 116 within the computerized device 110.

While this invention has been particularly shown and described with reference to preferred embodiments thereof, it will be understood by those skilled in the art that various changes in form and details may be made therein without departing from the spirit and scope of the invention as defined by the appended claims.

In one example, as illustrated and described with respect to FIG. 7, the detector 56 forms part of the calibrator 28. Such illustration and description is by way of example only. In an alternate arrangement, the calibrator 28 utilizes an external detector (e.g., a detector external to) the calibrator. For example, the calibrator 28 may utilize the analyzer 26 of the system 20 to perform the functions of the detector 56 described above.

FIG. 7 illustrates the detector 56 as having a single controller 64 configured to operate components of the calibrator (e.g., the elemental mercury source 50, the reactor heater 60, the oxidizing component source 52, and the oxidizing component source heater 62). Such illustration is by way of example only; in another arrangement the calibrator 28 includes separate controllers each performing one or more functions of the single controller 64 described above.

As indicated above, during operation, elemental mercury 66 flows from the elemental mercury source 50 to the reactor 54 via the conduit 58. Also during operation, the oxidizing component 68, such as chlorine gas, flows from the oxidizing component source 52 to the reactor 54 via the conduit 59. In another arrangement, the conduit 58 flows elemental mercury 66 past the oxidizing component source 52 to the reactor 54. The oxidizing component source 52 delivers the oxidizing component 68 to the reactor 54 by way of passive diffusion. Passive diffusion of the oxidizing component 68 limits or eliminates the need for a pump to force or draw the oxidizing component 68 from the oxidizing component source 52 and into the reactor 54.

FIG. 7 illustrates an arrangement of the calibrator 28 as including the elemental mercury source 50, the oxidizing component source 52, and the reactor as a single "unit". In one arrangement, the elemental mercury source 50 and the oxidizing component source 52 are located at two separate locations. For example, the elemental mercury source 50 can be located within an instrument rack while the oxidizing component source 52 is located in or within proximity to the probe 22.

Figure 11:
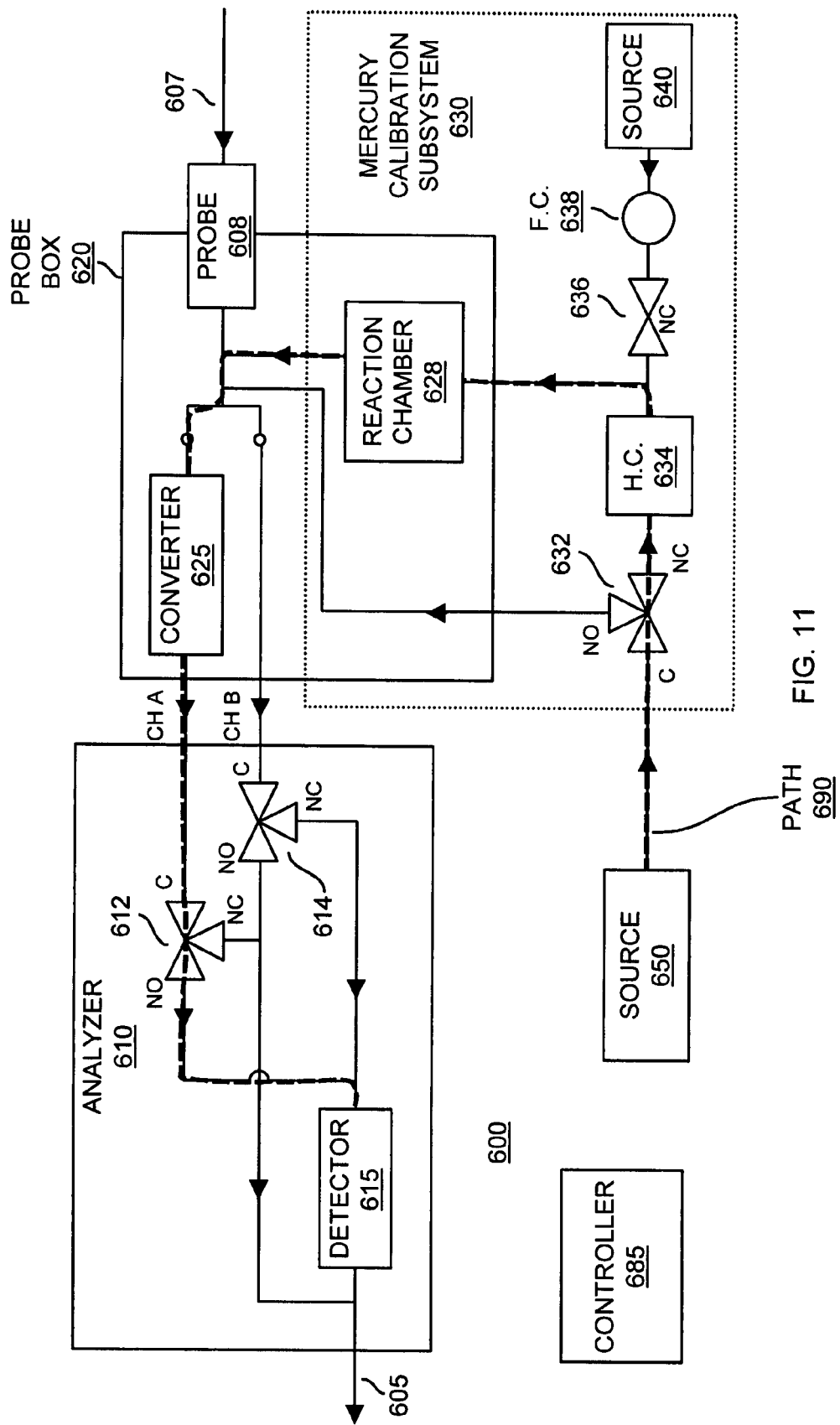
FIGS. 11-16 are schematics of a mercury monitoring system illustrating different flow paths employed for calibration/integrity checks in response to elemental and oxidized mercury and for monitoring mercury in flue gases according to embodiments herein.

FIG. 11 is a diagram illustrating a mercury monitoring system 600 with a calibrator according to embodiments herein.

As shown, mercury monitoring system 600 includes an analyzer 610, a probe box 620, mercury calibration subsystem 630, controller 685, and mercury source 650. Probe box 620 includes probe 608, converter 625, and reaction chamber 628 (e.g., a reactor). Analyzer 610 includes detector 615, valve 612, and valve 614. Mercury calibration subsystem 630 includes reaction chamber 628, valve 632, humidity controller 634, valve 636, flow controller 638, and oxidizer source 640.

Mercury monitoring system 600 includes flow conduits (e.g., pipes, tubes, etc.) connecting one element to another. Such conduits permit a gas sample from mercury source 650 (e.g., a first element) to pass to valve 632, from valve 632 to humidity controller 634, and so on. A vacuum pump (not shown) is included downstream of the analyzer 610 to draw gas samples through the monitoring system 600 and leave as exhaust 605. According to one configuration, the vacuum pump simultaneously draws a gas sample (e.g., from flue gas sample 607 such as that obtained from a smokestack or mercury calibration subsystem 630) through both channels A and B. However, the valves 612 and 614 are set such that only one of the channels is directed to detector 615 at a time. Accordingly, the detector 615 can be used to measure elemental mercury present in a gas sample on either channel A or channel B.

The mercury monitoring system 600 can be selectively configured by controller 685 to receive a gas sample produced by the mercury calibration subsystem 630 or receive flue gas 607 (e.g., exhaust from an industrial facility that potentially includes pollutants) via probe 608, one end of which protrudes into a smoke stack to receive the flue gas sample 607, the other end of which is encased in probe box 620 to selectively direct the flue gas sample 607 along channels A and B. Probe 608 can include an inertial filter, conditioners, temperature sensors, etc.

To ensure accurate analysis of flue gas 607, the mercury monitoring system 600 is initially calibrated and tested as discussed in FIGS. 11-16. The mercury monitoring system 600 can be occasionally or periodically calibrated (e.g., tested once a day, week, etc.) with one or more gas samples provided by the mercury calibration subsystem 630 to ensure the integrity of the mercury monitoring system 600. After calibration, the mercury monitoring system 600 can be used to monitor elemental mercury and oxidized mercury in flue gas sample 607, as discussed in FIGS. 19 and 20.

Referring again to FIG. 11, controller 685 of the mercury monitoring system 600 selectively controls a switching of a selected gas sample (e.g., a flue gas sample 607 from a probe 608 which extracts the sample from a stack, or flue, or a calibration sample from mercury calibration subsystem 630) between first and second flow paths (such as channel A and channel B) to detector 615. The different possible flow paths of mercury monitoring system 600 are defined by setting valve 612, valve 614, valve 632, and valve 636. Valves can be manually or automatically controlled. According to one configuration, controller 685 sets up different gas flow paths by sending electrical signals along electrical lines (not shown) to open and close the above mentioned valves in mercury monitoring system 600.

Port C of valves 612, 614, 632 serve as a collector or input. The output of valve 612, valve 614, and valve 632 can be configured to enable a flow from input port C to the output of port NC or port NO based on control signals from controller 685. Valve 636 can be turned on and off (by controller 685) to enable a flow of gas (e.g., an oxidizing component such as chlorine gas) to reaction chamber 628. Accordingly, the controller 685 can effectively direct a gas sample along any of multiple appropriate flow paths to detector 615.

Figure 12:
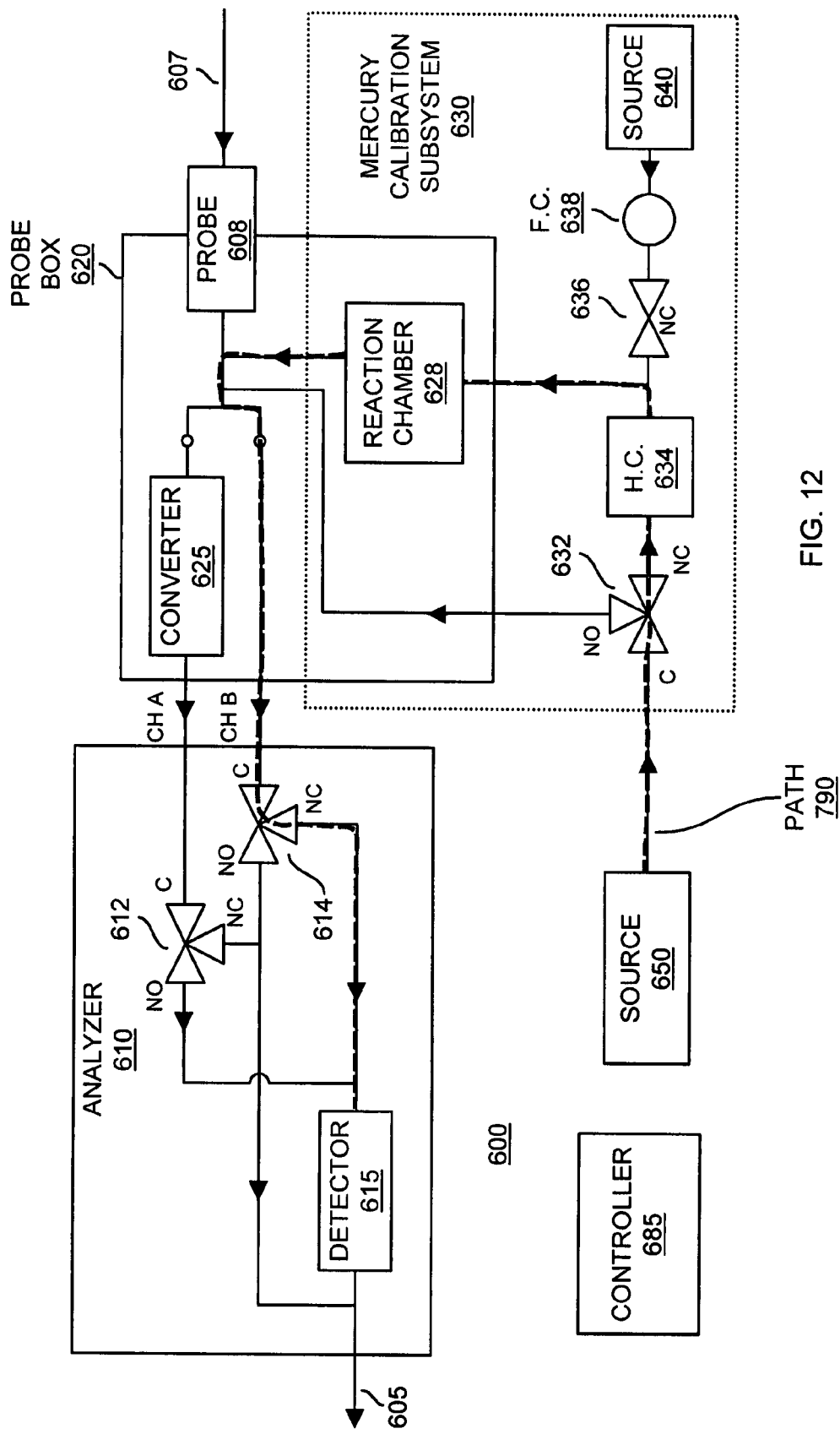

Note that a gas sample (whether from mercury calibration subsystem 630 or flue gas 607) can simultaneously flow through both channels A and B. However, during operation, only one of the channels is directed to pass the gas sample to the detector 615 while the other passes through analyzer 610 as exhaust 605 without passing through detector 615. The output of detector 615 also leaves the analyzer 610 as exhaust 605. In other words, while controller 685 sets valve 612 to direct a gas sample on channel A from input port C to output port NO, the controller 685 simultaneously sets valve 614 to direct the gas sample on channel B from input port C to output port NO. While in this mode setting (as shown in FIG. 11), the output of detector 615 and gas sample on channel B passing through valve 614 combine to form exhaust 605. Conversely, while controller 685 sets valve 612 to direct a gas sample on channel A from input port C to output port NC (bypassing detector 615), the controller simultaneously sets valve 614 to direct the gas sample on channel B from input port C to output port NC. While in this mode setting (as shown in FIG. 12), the output of detector 615 and gas sample on channel A passing through valve 612 combine to form exhaust 605.

Now more particularly, to direct an elemental mercury calibration gas sample from source mercury 650 (e.g., mercury vapor or gas) to detector 615 on flow path 690, the controller 685 sets valve 632 and valve 612 so that the gas sample flows through valve 632, humidity controller 634, reaction chamber 628, converter 625, and valve 612 to detector 615. Accordingly, controller 685 selectively delivers different gas samples (e.g., flue gas 607 or calibration gas samples from mercury calibration subsystem 630) along channels A and B to detector 615. According to one configuration, the controller 685 repeatedly switches between delivery of different gas samples on the first channel and the second channel to the detector to verify at least one of: i) an ability of the detector to detect elemental mercury gas, and ii) an ability of the converter to convert oxidized mercury into elemental mercury gas.

The humidity controller 634 disposed within subsystem 630 modifies (e.g., increases or decreases) a relative humidity of the calibration gas sample so that the relative humidity of a mercury gas sample is greater than 20%, such as within a specified range of between 50% and 80%. The corresponding temperature of gas sample at humidity controller 634 may be in the range of 15-35 or, in other embodiments, 15-45 degrees Celsius.

Humidifying (e.g., water vapor) to a mercury calibration gas sample enhances a flow of the gas sample (e.g., oxidized mercury) along a flow path. In other words, adjusting the relative humidity of the gas sample ensures that a majority of the elemental mercury and/or oxidized mercury in a gas sample does not stick to the walls of pipes, conduits, filters, etc. defining a flow path to detector 615. According to one configuration, the humidity controller 634 (e.g., a permeation wetter or dryer) includes a vessel of liquid water that removes or adds water to the gas sample.

Also, note that the humidity controller 634 can modify a relative humidity associated with a calibration gas sample to simulate a relative humidity of a flue gas 607 that is tested for presence of mercury. Accordingly, measurements associated with testing the flue gas 607 are more accurate because the mercury monitoring system 600 is calibrated under similar environmental conditions. In other words, the gas sample provided for calibration can be controlled to have a similar amount of water as that of a flue gas 607 under test.

As discussed above, probe box 620 of the mercury monitoring system 600 includes a converter 625 that converts any or most oxidized mercury gas (as by heating it to an elevated temperature such as 750 degrees Celsius) into elemental mercury gas. An output of the converter 625 in flow path 690 passes through valve 612 and feeds into the detector 615. Detector 615 detects an amount of elemental mercury gas in a received gas sample along flow path 690. In this example, the sample gas comes from source 650 such as a gas cylinder of elemental mercury of known concentration or a vapor generator, which evaporates liquid mercury into elemental mercury gas, either of which provides a known concentration of elemental mercury gas for use by mercury monitoring system 600.

When flow path 690 is selected by controller 685 as shown in FIG. 11, the detector 615 detects a presence of a total amount of mercury in a gas sample from source 650 including i) an original amount of elemental mercury in the gas sample from source 650 as well as ii) any elemental mercury derived from conversion of oxidized mercury into elemental mercury by the converter 625. However, source 650 typically provides little or no oxidized mercury. (Recall that during any calibration test or any analysis of flue gas sample 607, the mercury monitoring system 600 can direct flow simultaneously through both channels A and B; typically, however, only the flow in one channel is directed into the detector 615—e.g., only the flow in channel B goes to detector 615 during operation per flow path 790 illustrated in FIG. 12.)

FIG. 12 illustrates a calibration flow path of the mercury monitoring system 600 according to embodiments herein. As shown, similar to the flow path 690 as discussed above in FIG. 11, flow path 790 of the mercury monitoring system 600 as shown in FIG. 12 also directs a gas sample from source 650 to the detector 615. However, flow path 790 (i.e., including channel B) bypasses the converter 625. Accordingly, if any oxidized mercury were present in the gas sample from source 650, it would not be converted into elemental mercury.

As discussed above, the mercury monitoring system 600 is at least occasionally calibrated (e.g., tested) with gas samples provided by the mercury calibration subsystem 630. For example, to calibrate the detector 615 of the mercury monitoring system 600, the mercury calibration subsystem 630 produces a gas sample from source 650 including a known concentration of elemental mercury gas with little or no oxidized mercury in the gas sample. The controller 685 of the mercury monitoring system 600 initiates switching between delivering the first gas sample from source 650 to the detector 615 on flow path 690 in FIG. 11 and flow path 790 in FIG. 12. Readings by the detector 615 for a gas sample received on flow path 690 and flow path 790 should be substantially the same because the gas sample includes little or no oxidized mercury.

The detector 615 is calibrated based on the readings for the gas sample received from the source 650 since the detector 615 should properly measure the known concentration of elemental mercury gas provided by the source 650. Note that calibration of the detector 615 can include hardware and/or software adjustments so that future readings of the detector accurately reflect how much elemental mercury is in a gas sample. According to one configuration, the detector 615 is a linear device and calibration at a single elemental mercury concentration is sufficient for proper operation. However, note that detector 615 can be calibrated at multiple different elemental mercury concentrations if necessary.

Assume that the source 650 provides a gas sample having a known concentration of gaseous elemental mercury of 10 micrograms per cubic meter. As shown by flow paths 690 and 790 respectively in FIGS. 11 and 12, the controller 685 repeatedly switches (e.g., approximately at one minute intervals) between channel A and channel B, and in both cases a concentration of gaseous elemental mercury of 10 micrograms per cubic meter is detected. Detector 615 can include an integrator circuit that is sampled one or more times during the one-minute interval when the gas sample travels along a selected flow path. Upon switching to the other channel, the integrator associated with detector 615 is reset.

Figure 13:
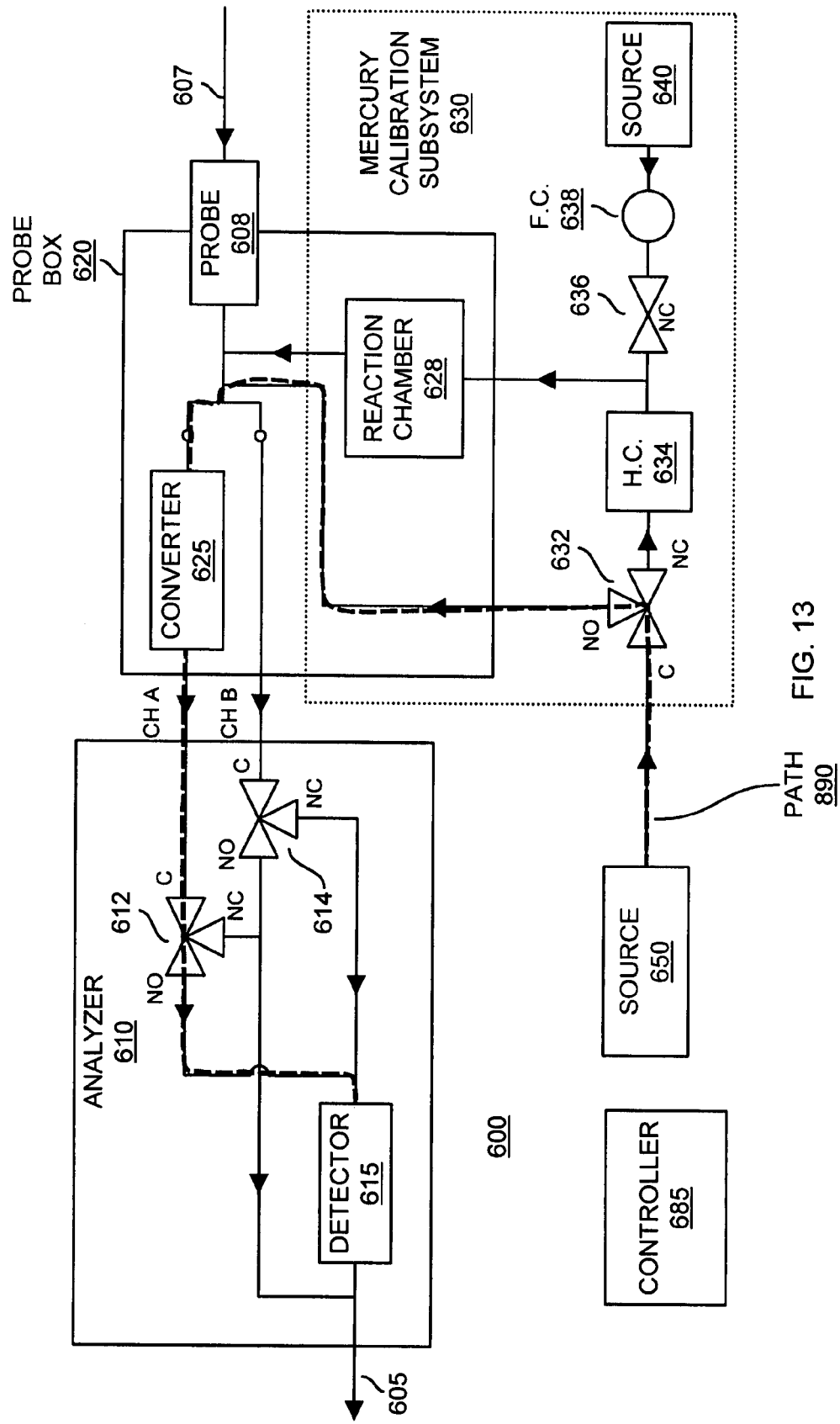
Figure 14:
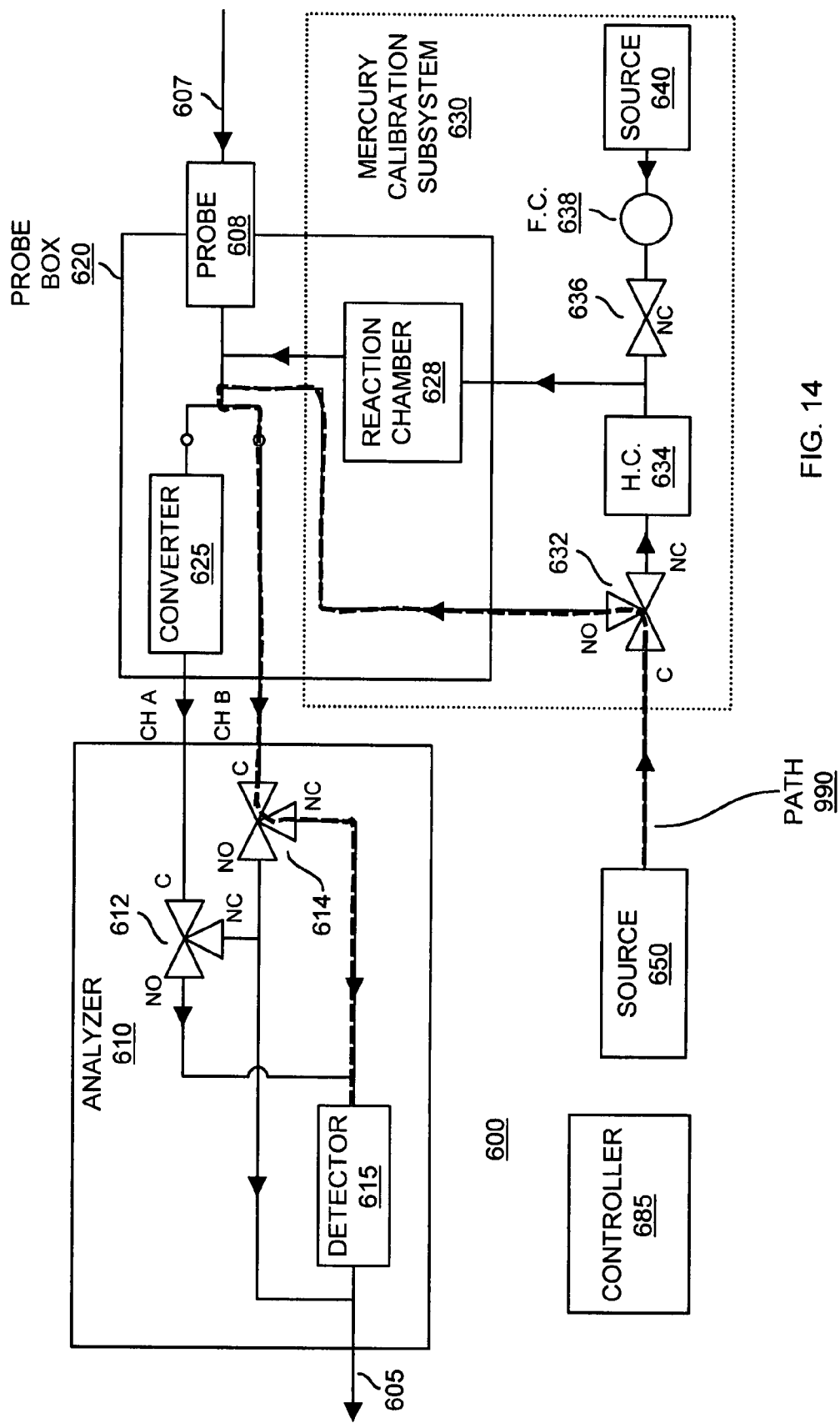

FIGS. 13 and 14 illustrate the same system 600 as in FIGS. 11 and 12 but operating with an alternate pair of flow paths in lieu of those shown in FIGS. 11 and 12, wherein mercury gases from source 650 flows to analyzer 610 without passing through humidity controller 634 and reaction chamber 628. For example, as shown in FIG. 13, the controller 685 can set valve 632 and valve 612 to direct a gas sample along flow path 890 from source 650 through valve 632, converter 625, and valve 612 to detector 615. As shown in FIG. 14, the controller 685 can set valve 632 and valve 614 to direct a gas sample along flow path 990 from source 650 through valve 632 and valve 614 to detector 615.

Assume that the source 650 provides a gas sample having a known concentration of gaseous elemental mercury of 10 micrograms per cubic meter as discussed above. As shown by flow paths 890 and 990 respectively in FIGS. 13 and 14, the controller 685 repeatedly switches (e.g., approximately every minute or so) between channels A and channel B and in both cases a known concentration of gaseous elemental mercury of 10 micrograms per cubic meter is detected. If necessary, the detector 615 is calibrated as discussed above in FIGS. 11 and 12.

Figure 15:
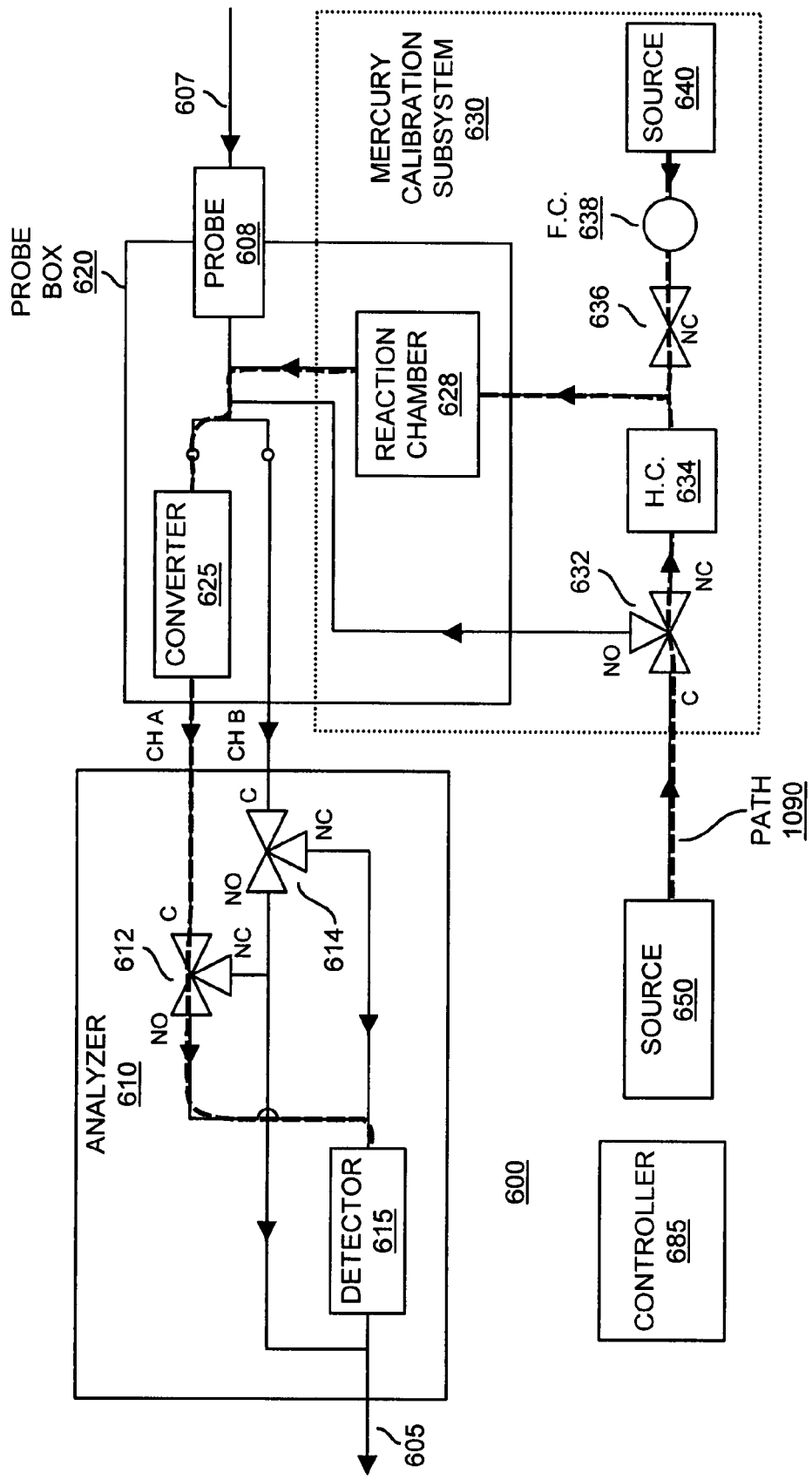
Figure 16:
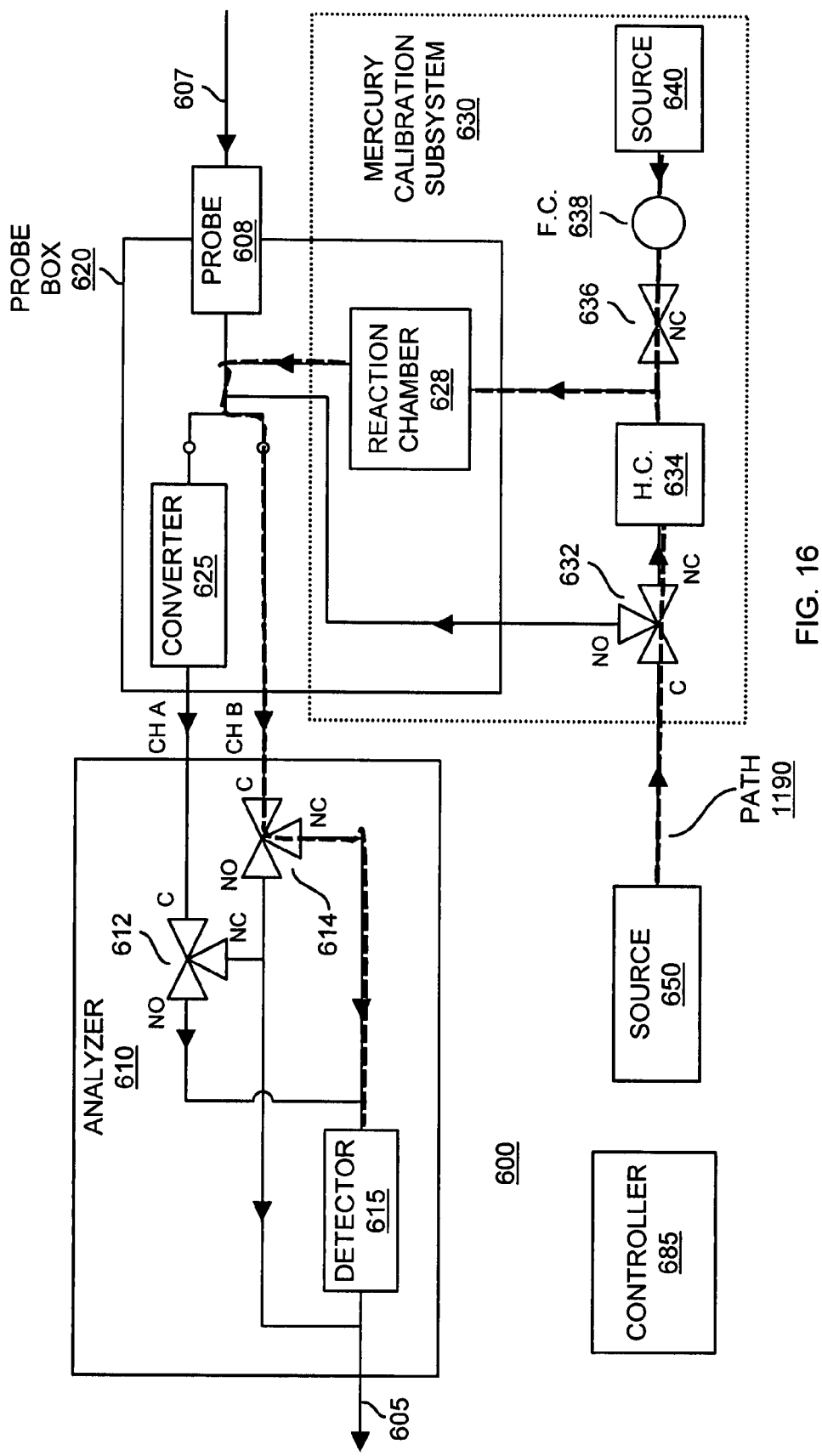

FIGS. 15 and 16 illustrate the system 600 operating with a pair of flow paths for testing response to oxidized mercury, including testing for a conversion efficiency associated with converter 625 according to embodiments herein. This efficiency test is generally performed after calibrating the detector 615 as mentioned above.

Figure 19:
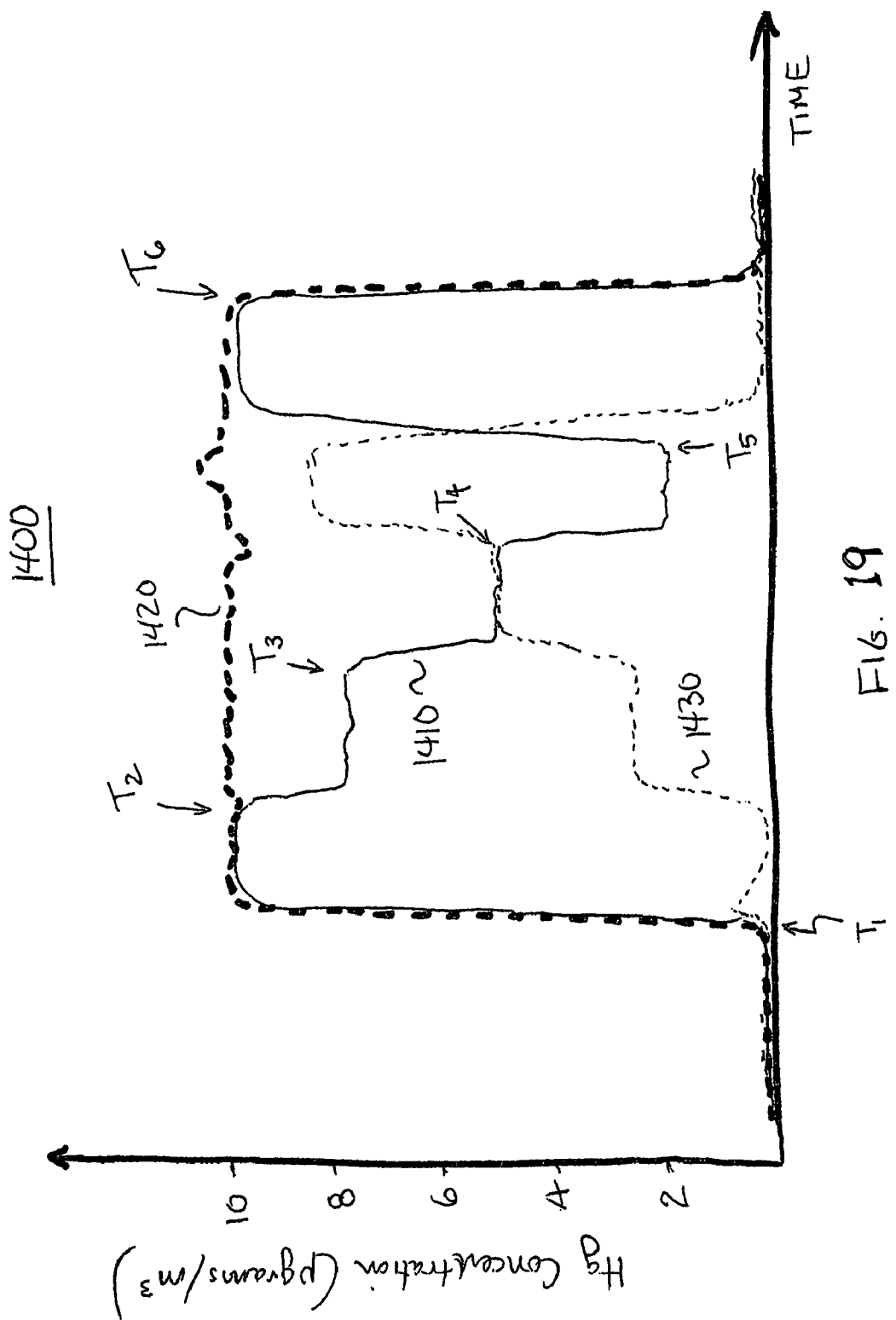
Figure 20:
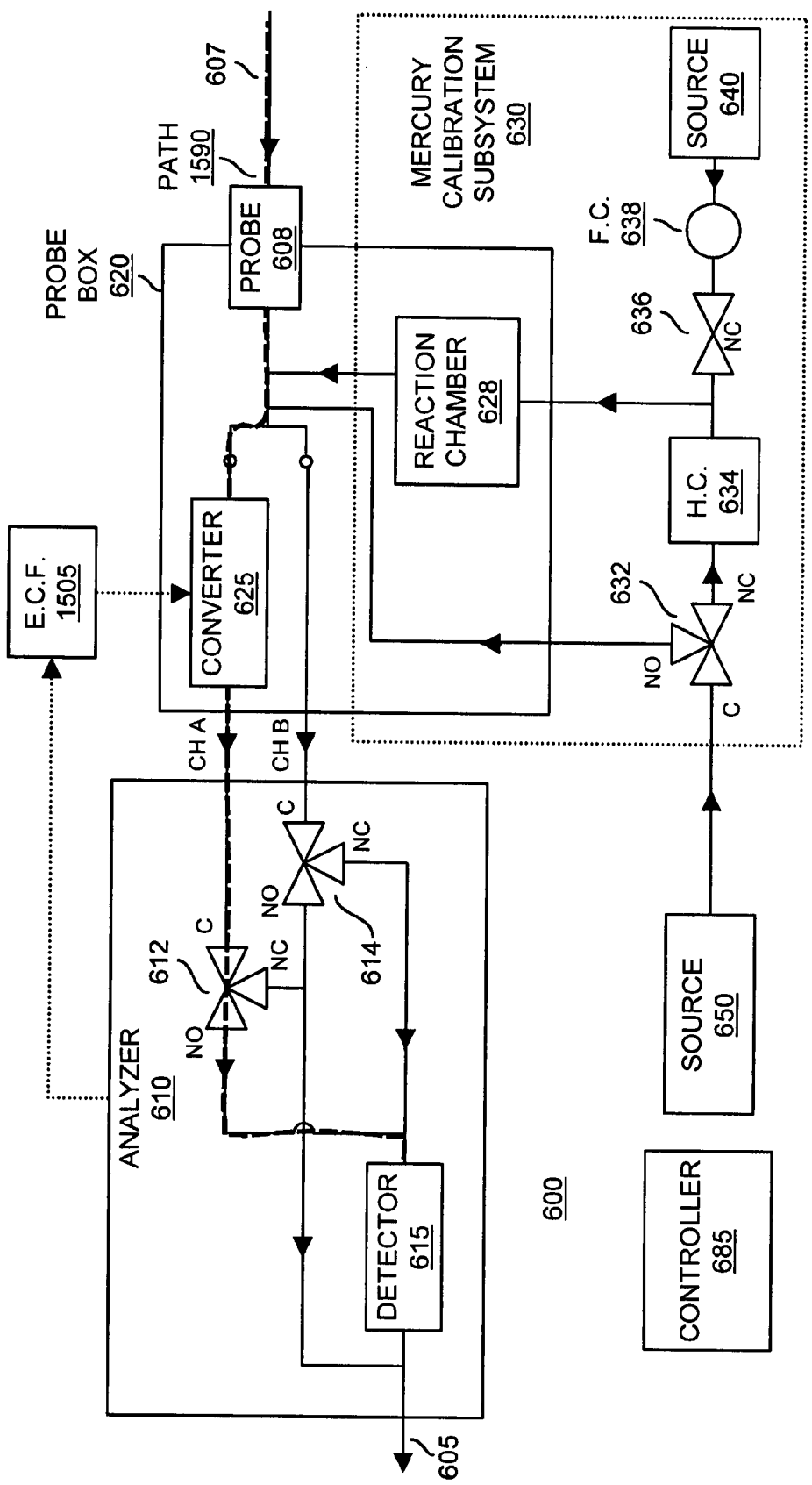
FIGS. 20-21 are schematics of a mercury monitoring system illustrating different flow paths employed for calibration/integrity checks in response to elemental and oxidized mercury and for monitoring mercury in flue gases according to embodiments herein.

The efficiency of converter 625 can be occasionally tested to ensure its proper operation. Otherwise, the mercury monitoring system 600 and, more specifically, the detector 615 may not be able to measure the total mercury present in a flue gas 607 when so tested (as shown in FIGS. 19 and 20). As an example, a flue gas 607 under test may include a high level of oxidized mercury (e.g., mercury halide) and little to no elemental mercury. If the converter 625 does not efficiently (e.g., completely) convert substantially all of the mercury halide in the flue gas 607 to elemental mercury, then the detector 615 will be unable to accurately detect the total amount of mercury in the flue gas 607 sample. This measurement can be quite important because governmental standards require that a total amount of mercury present in a flue gas sample be maintained below a threshold value. Operating mercury monitoring system 600 with a faulty converter 615 (that does not properly convert oxidized mercury into elemental mercury) could violate this regulation.

To test the efficiency (e.g., an ability of the converter to convert oxidized mercury in the gas sample to elemental mercury) of the converter 615, the mercury calibration subsystem 630 produces gas sample in reaction chamber 628 (e.g., reaction chamber) by reacting elemental mercury gas received from source 650 with an oxidizing component received from source 640. Flow controller 638 and valve 636 control how much oxidizer gas is delivered to reaction chamber 628. Reaction chamber 628 can be heated to a temperature such around 400 degrees Celsius to enhance a conversion of elemental mercury gas into oxidized mercury (e.g. a mercury halide gas).

Recall that the elemental mercury gas received from source 650 can have a known concentration (e.g., 10 micrograms of mercury/cubic meter). The oxidizing component from source 640 preferably converts a portion of the known concentration of elemental mercury provided by source 650 into oxidized mercury gas such that the gas sample in reaction chamber 628 includes a mixture of an unknown concentration of elemental mercury gas and an unknown concentration of oxidized mercury gas. (Complete conversion of the elemental mercury in the gas sample to oxidized mercury is generally not desirable but could occur if the flow controller 638 were to pass an excessive amount of oxidizing agent through valve 636 to reaction chamber 628.)

The controller 685 of the mercury monitoring system 600 selectively switches between delivering the gas sample produced in reaction chamber 628 to detector 615 on flow path 1090 and flow path 1190 as shown respectively in FIG. 15 and FIG. 16. Similar to the technique as mentioned above, the controller 685 switches between flow paths to detector 615 at desired times such as every minute or so. An output of the detector 615 can feed into an integrator that is sampled at a rate such as every several seconds.

Periodically switching between receiving a gas sample at detector 615 from channel A and channel B (e.g., on flow paths 1090 and 1190) enables the mercury monitoring system 600 to continuously identify (e.g., on a continuous basis via use of the same detector) an amount of elemental mercury gas from source 650 as well as an amount of oxidized mercury gas produced in reaction chamber 628.

According to one configuration, an analyzer 610 of the mercury monitoring system 600 utilizes sample measurements from the detector 615 at appropriate times to measure an amount of original elemental mercury in the gas sample as received on channel B (e.g., flow path 1190 as shown in FIG. 16). After switching to receiving the gas sample on channel A (e.g., flow path 1090 as shown in FIG. 15), the analyzer 610 utilizes sample data from detector 615 to measure a total amount of mercury in the gas sample (rather than only the elemental mercury in the gas sample as on channel B) because the gas sample passes through converter 625, which converts any oxidized mercury into elemental mercury.

Based on repeated switching between channels and taking continuous measurements on channels A and B for a given gas sample produced in reaction chamber 628, the mercury monitoring system 600 can deduce how much oxidized mercury (e.g., mercury halide) is present in a gas sample. For example, while receiving a gas sample on channel B (e.g., flow path 1190 as shown in FIG. 16), the detector 615 measures an amount of elemental mercury in the gas sample. While receiving the gas sample on channel A (e.g., flow path 1090 as shown in FIG. 15), the detector 615 measures a total amount of mercury in the gas sample. The analyzer 610 of mercury monitoring system 600 deduces an amount of oxidized mercury in the gas sample based on a difference between the two measurements.

As briefly mentioned above, the mercury calibration subsystem 630 can include a flow controller 636 that controls a rate of flow of the oxidizing component received from source 640 to limit how much of the elemental mercury provided from gas source 650 is converted into the oxidized mercury gas in the reaction chamber 628. For example, the flow controller 638 can control and provide enough oxidizing component (e.g., a component such as chlorine, bromine, ozone, nitrate, etc.) to convert a portion of elemental mercury (e.g., an original concentration of 10 micrograms/cubic meter) from source 650 into oxidized mercury so that the output of the reaction chamber 628 contains approximately 25% elemental mercury and 75% oxidized mercury.

When this gas sample (e.g., assume that the gas from source 650 has a concentration of 10 micrograms of mercury/cubic meter) produced in reaction chamber 628 is switched between flow path 1090 and flow path 1190, the detector 615 should detect a presence of 2.5 micrograms/cubic meter on flow path 1190 and 10 micrograms/cubic meter on flow path 1090 since (ideally all of) the oxidized mercury in the gas sample from reaction chamber 628 will be converted into elemental mercury on the flow path 1090 (e.g., channel A). Thus, detector 615 measurements associated with flow path 1090 should indicate the total amount of mercury present in the gas sample.

If the detector 615 detects that the gas sample on flow path 1090 (e.g., the total mercury measurement channel which includes the converter 625) does not have an associated concentration of elemental mercury substantially equal to the known concentration of elemental mercury gas (e.g., 10 micrograms/cubic meter) initially in the gas sample as provided by source 650, then the converter 625 has failed to properly convert the oxidized mercury in the gas sample back to elemental mercury gas. If the error is less than a threshold value, the mercury monitoring system 600 produces and utilizes a correction factor for adjusting future measurements when sampling on channel A. In other words, if the reading of a total amount of elemental mercury on channel A is off by a fairly small amount, the mercury monitoring system 600 implements a correction factor to account for an inability to convert all oxidized mercury into elemental mercury. Otherwise, the converter 625 may be faulty and need to be replaced.

As an example, assume that the detector 615 measures the total mercury on channel A as 9.5 micrograms/cubic meter and an amount of elemental mercury of 2.5 micrograms/cubic meter on channel B. Recall that the reading on channel A should be 10 micrograms of mercury/cubic meter because this is the total amount of mercury in the gas sample. This means that the converter 625 likely only converted 7.0 micrograms/cubic meter of the oxidized mercury rather than all 7.5 micrograms/cubic meter in the gas sample. Thus, the efficiency of converter 625 (at this concentration) is 7/7.5 or 93.3%. The correction factor of 1.0714 (e.g., 1/0.9333) can be applied to future measurements in which the concentration of oxidized mercury is around 7.0 micrograms of mercury/cubic meter. For example, when measuring flue gas 607, if a measurement by detector 615 indicates a presence of 6.8 micrograms of mercury/cubic meter on channel A, the actual reading is more likely a concentration of (6.8×1.0714), or 7.285 micrograms of mercury/cubic meter due to the inability of the converter device to completely convert all oxidized mercury to elemental mercury in a respective gas sample.

Figure 17:
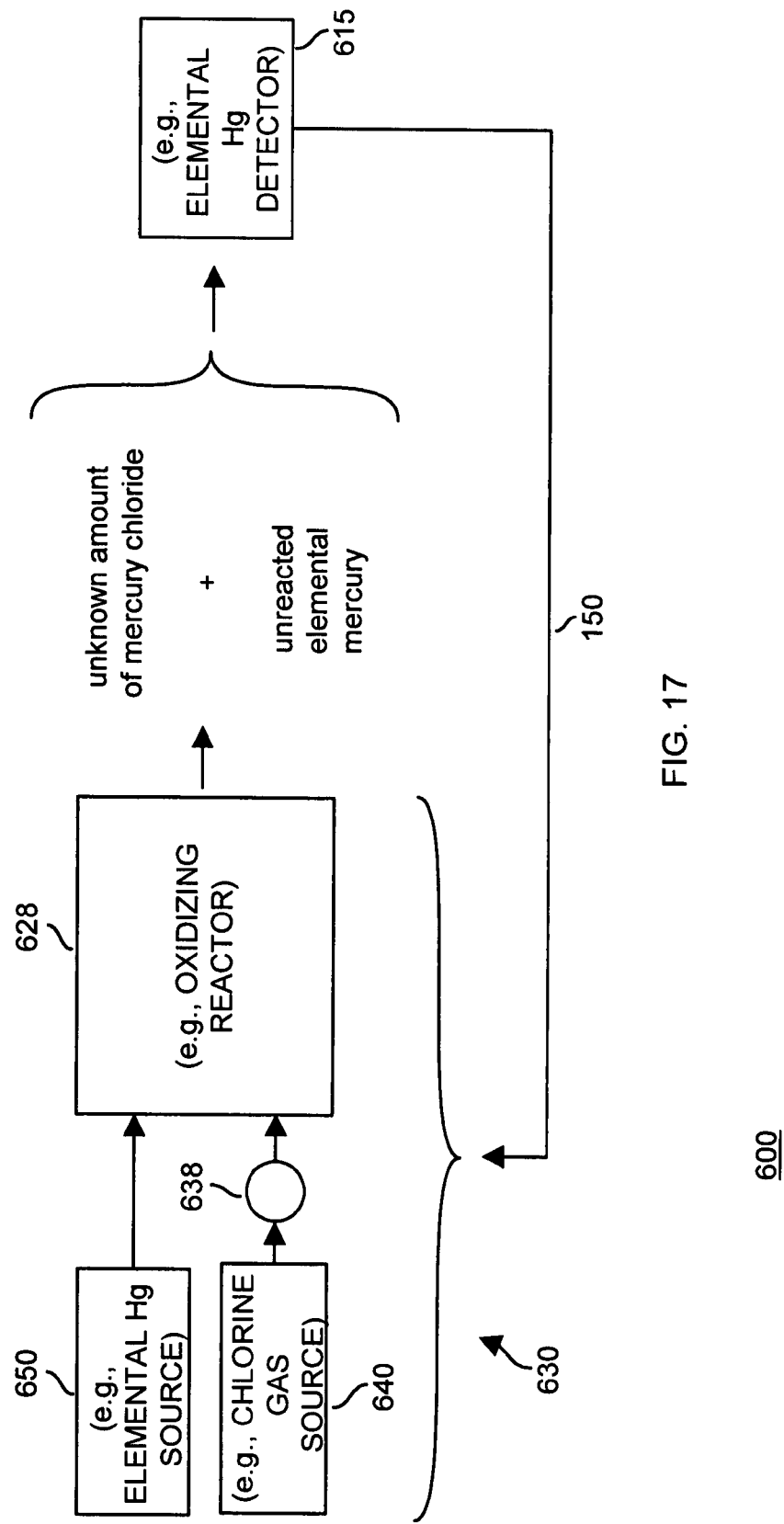
FIG. 17 is a diagram illustrating generation of a gas sample with oxidized mercury and elemental mercury for calibration according to embodiments herein.

FIG. 17 is a diagram illustrating details of how mercury calibration subsystem 630 produces oxidized mercury for system calibration according to embodiments herein. The mercury calibration subsystem 630 for producing the mercury halide $HgCl_2$ includes an elemental mercury source (e.g., source 650) and a chlorine gas source (e.g., source 640), which feed mercury and chlorine vapors into a reaction chamber 628 (e.g., an oxidizing reactor). The reaction chamber 628 in turn produces an unknown amount of mercury chloride and an amount or remainder of un-reacted elemental mercury. For reasons explained below, one or more parameters such as the amount of chlorine directed to the reaction chamber 628 (e.g., oxidizing reactor) are adjusted via flow controller 638 so there is always an excess of elemental mercury leftover in the gas sample. Thus, the output of the reactor (reaction chamber 628) includes some amount of un-reacted elemental mercury (e.g., about 15-85% of the elemental mercury gas supplied from source 650). Making sure that a portion of the elemental mercury gas supplied from 650 is not converted into mercury halide can be accomplished by an automatic feedback mechanism 150, or manually, with any needed adjustments based on the amount of elemental mercury detected by detector 615.

To measure and control the amount of excess elemental mercury and to calculate, deduce or infer the unknown amount of $HgCl_2$ formed in the reaction chamber 628, the mercury monitoring system 600 includes a detector 615 and a computational device such as a computer, either within or separate from detector 615, to detect elemental mercury. In particular, elemental mercury detector 615 measures the amount of un-reacted elemental mercury output from reaction chamber 628 on channel B as discussed above. The detector 615 also measures the total amount of elemental mercury (i.e., the mercury provided by the source 650) by use of a bypass channel (channel A) through which the output of reaction chamber 628 is (periodically) passed and which includes a converter 625 to convert oxidized mercury to elemental mercury as previously discussed.

The difference between the known concentration of elemental mercury provided by the elemental mercury source 650 (known initially from parameters of the source 650 and/or measured by the detector 615 from the output of channel A) and the measured amount of un-reacted elemental mercury output from reaction chamber 628 indicates how much mercury chloride was produced in the reaction chamber 628. In other words, the amount of mercury chloride produced is based on post-reaction detection and analysis and is unknown until then. This deduced or estimated amount of mercury chloride sample is used for calibrating the mercury monitoring system 600 for oxidized mercury.

According to one configuration, the mercury monitoring system 600 intentionally does not completely oxidize all elemental mercury supplied to the reaction chamber 628, for at least two reasons: i) an indirect determination of oxidized mercury by subtraction provides a better representation and control of the oxidized mercury produced, and ii) to assure oxidation of all mercury would require an excessive amount of chlorine, and the excess chlorine might subsequently react with (re-oxidize) elemental mercury in the bypass channel or elsewhere in the system and interfere with accurate detection of elemental mercury. (Excess chlorine could be removed or scrubbed by a filter, but even then its presence would present a risk of breakthrough and/or a reduction in useful filter life.)

As indicated earlier, the mercury monitoring system 600 can include control, either manually or by a feedback loop 150, to ensure that only a portion (e.g., about 10-90%) of elemental mercury supplied by source 650 to the reaction chamber 628 is converted into mercury chloride. Thus, if the calculated amount of mercury chloride is below a target value, system parameter settings can be modified (e.g., to increase the amount of chlorine gas provided by source 640, raise a temperature of reaction chamber 628, etc.) so as to increase the amount of elemental mercury converted into mercury chloride. Conversely, if more than a desired amount of elemental mercury is being converted into mercury chloride in reaction chamber 628, system parameter settings of mercury monitoring system 600 can be modified (e.g., to decrease an amount of chlorine gas provided by source 640, decrease a temperature of reaction chamber 628, control a flow using valve 638, etc.) to reduce the amount of conversion.

Figure 18:
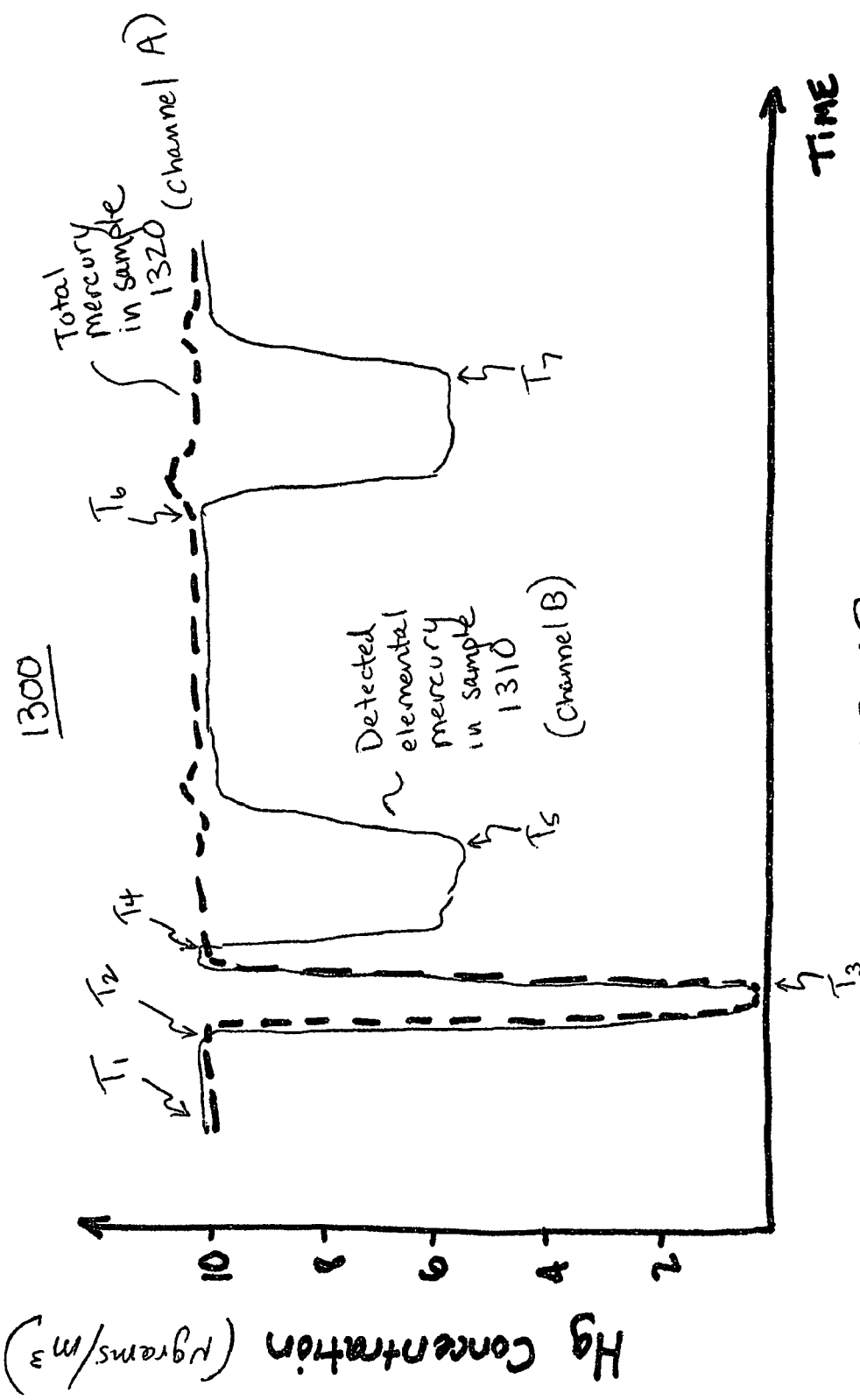
FIGS. 18 and 19 are graphs illustrating detection of elemental mercury and total mercury in a gas sample according to embodiments herein.

FIG. 18 is a graph 1300 illustrating hypothetical results associated with testing of a mercury monitoring system 600 according to embodiments herein. Graph 1300 represents a display of measurements produced by detector 615 while switching between detecting elemental mercury in flow path 1090 (as shown in FIG. 15) and flow path 1190 (as shown in FIG. 16) over time. Plot 1310 on graph 1300 represents the detected elemental mercury in a sample received on channel B as detected by detector 615. Plot 1320 on graph 1300 represents the detected total elemental mercury in a sample received on channel A as detected by detector 615. A time difference between time T1 and time T2 or between T1 and T6 can be on the order of a half hour. During this time span, controller 685 of mercury monitoring system 600 controls valves (e.g., valve 612, valve 614, valve 632, and valve 636) and flow controller 638 as follows:

i) At time T1, the controller 685 enables a flow of elemental mercury gas (e.g., a known concentration of 10 micrograms/cubic meter) from source 650 through reaction chamber 628 to detector 615 on flow path 1090 and flow path 1190. Source 640 is disabled from providing an oxidizing gas by shutting off valve 636. Between time T1 and T2, both channel A and channel B measure the same level of approximately 10 micrograms/cubic meter of elemental mercury in the gas sample.

ii) At time T2, the controller 685 disables a flow of elemental mercury gas (e.g., a known concentration of 10 micrograms/cubic meter) from source 650 through reaction chamber 628 to detector 615 on flow paths 1090 and 1190. Source 650 is disabled from providing mercury gas by shutting off valve 632. Between time T2 and T3, both channel A and channel B eventually measure no elemental mercury in the calibration gas sample.

iii) At time T3, the controller 685 re-enables a flow of elemental mercury gas (e.g., a known concentration of 10 micrograms/cubic meter) from source 650 through 632 and reaction chamber 628 to detector 615 on flow paths 1090 and 1190. Source 640 is disabled from providing an oxidizing gas by shutting off valve 636. Between time T3 and T4, both channel A and channel B eventually measure the same level of approximately 10 micrograms/cubic meter of elemental mercury in the gas sample again.

iv) At time T4, the controller 685 continues to enable a flow of elemental mercury gas (e.g., a known concentration of 10 micrograms/cubic meter) from source 650 through reaction chamber 628 to detector 615. The controller 685 controls valve 636 and flow controller 638 to enable source 640 to provide enough oxidizing gas to convert about 40% of the elemental mercury gas in reaction chamber 628 (as provided by source 650) into oxidized mercury (e.g., mercury chloride). Between time T4 and T5, the controller 685 controls the valves in mercury monitoring system 600 to switch between measuring a level of elemental mercury in the sample gas from channel A and channel B as previously discussed. Between time T4 and T5, plot 1320 of graph 1300 reflects that the total amount of elemental mercury received on channel A remains approximately constant. Between time T4 and T5, plot 1310 of graph 1300 reflects that the amount of elemental mercury gas in the sample as received on channel B decreases as a result of a conversion of elemental mercury from source 650 into oxidized mercury.

v) At time T5, the controller 685 continues to enable a flow of elemental mercury gas (e.g., a known concentration of 10 micrograms/cubic meter) from source 650 through reaction chamber 628 to detector 615. The controller 685 controls valve 636 and flow controller 638 to disable source 640 from delivering oxidizing gas to reaction chamber 628. Accordingly, between time 15 and T6, none of the gas from source 650 is converted into oxidized mercury, and thereafter until time T6 as shown by plots 1310 and 1320, both elemental mercury readings on channel A and channel B measure the same level of approximately 10 micrograms/cubic meter of elemental mercury in the gas sample.

vi) At time T6, the controller 685 continues to enable a flow of elemental mercury gas (e.g., a known concentration of 10 micrograms/cubic meter) from source 650 through reaction chamber 628 to detector 615. The controller 685 controls valve 636 and flow controller 638 to again enable source 640 to provide enough oxidizing gas to convert about 40% of the elemental mercury gas in reaction chamber 628 (as provided by source 650) into oxidized mercury (e.g., mercury chloride). Between time T6 and T7, the controller 685 controls the valves in mercury monitoring system 600 to switch between measuring a level of elemental mercury in the sample gas from channel A and channel B as previously discussed. Between time T6 and T7, plot 1320 of graph 1300 reflects that the total amount of elemental mercury received on channel A remains approximately constant. Between time T6 and T7, plot 1310 of graph 1300 again reflects that the amount of elemental mercury gas in the sample as received on channel B decreases as a result of a conversion of elemental mercury from source 650 into oxidized mercury.

vii) At time T7, the controller 685 continues to enable a flow of elemental mercury gas (e.g., a known concentration of 10 micrograms/cubic meter) from source 650 to detector 615. The controller 685 controls valve 636 to disable source 640 from delivering oxidizing gas to reaction chamber 628. Accordingly, eventually none of the gas in reaction chamber 628 from source 650 is converted into oxidized mercury. As shown by plots 1310 and 1320 after time T7, both elemental mercury readings on channel A and channel B eventually measure the same level of approximately 10 micrograms/cubic meter of elemental mercury in the gas sample.

Additional embodiments herein include verifying efficiency of the converter 625 over a range of different concentrations of oxidized mercury. Note that an ideal converter device will be able to convert 100% of the oxidized mercury into elemental mercury gas regardless of the concentration of oxidized mercury. However, efficiency of converter 625 often varies depending on concentration of the oxidized mercury to be converted. Based on sampling of gases having different concentrations of oxidized mercury at different times, the mercury monitoring system 600 as discussed herein can identify appropriate correction factors to apply for different detected concentrations for more accurately determining actual concentrations of oxidized mercury in a flue gas sample.

As illustrated in the graph 1400 of FIG. 19 illustrating hypothetical operation, the mercury calibration subsystem 630 produces multiple different sample gases having different concentrations of oxidized mercury and elemental mercury for testing converter efficiency. Plot 1410 of graph 1400 represents measurements of an amount of elemental mercury in a gas sample as detected on channel B. Plot 1420 of graph 1400 represents measurements of total elemental mercury detected in the gas sample on channel A. Plot 1430 of graph 1400 represents a deduced amount of oxidized mercury present in the different gas samples produced by mercury calibration subsystem 630. The time span between time T1 and T6 represents a testing cycle of approximately a half hour to an hour of time. This can vary depending on the application. Recall again that controller 685 switches between delivery of sample gases in reaction chamber 628 on channels A and B to detector 615 each minute or so. The analyzer 610 can be configured to initiate operation of the detector 615 at multiple sample times during the test duration between T1 and T6 to test an ability of the converter to convert the different concentration levels of oxidized mercury in the gas sample into elemental mercury for each of the steps.

For example, similar to the techniques as discussed above in FIG. 18, the controller 685 of mercury calibration subsystem 630 controls a flow rate (via flow controller 638) of oxidizing component from source 640 for a first time duration between time T2 and time T3 so that the output of reaction chamber 628 includes a first set of concentrations of elemental mercury gas and oxidized mercury gas (e.g., 25% oxidized mercury and 75% elemental mercury). As discussed above, for this first time duration, the controller 685 switches between delivering the gas sample produced in reaction chamber 628 to the detector 615 on channel A (e.g., flow path 1090) and channel B (e.g., flow path 1190) to identify an amount of elemental mercury and oxidized mercury present in the gas sample.

Based on measurements by the detector on channel A and channel B, the analyzer 610 of mercury monitoring system 600 utilizes sample data produced by detector 615 to identify whether converter 625 efficiency falls below 100% for the given concentration of oxidized mercury (e.g., 25% oxidized mercury or 2.5 micrograms/cubic meter) in the gas sample. If necessary, the mercury monitoring system 600 or, more specifically, the analyzer 610 produces a correction factor associated with the converter device for the given concentration level so that future measurements of elemental mercury received on channel A are more accurate.

After testing the first gas sample (e.g., 25% oxidized mercury to 75% elemental mercury) for the first time duration between time T2 and time T3, the mercury calibration subsystem 630 controls a flow rate of oxidizing component from source 640 so that the output of reaction chamber 628 includes a second set of concentrations of elemental mercury gas and oxidized mercury gas (e.g., 50% oxidized mercury and 50% elemental mercury) for a second duration of time between time T3 and time T4. For this second time duration, the mercury monitoring system 600 switches between delivering the gas sample on channel A and channel B to the detector 615 so that the analyzer 610 can identify an amount of elemental mercury and oxidized mercury present in the second gas sample. Based on measurements by the detector 615, the mercury monitoring system 600 identifies whether converter efficiency falls below 100% for the given concentration of oxidized mercury (e.g., 5 micrograms/cubic meter) in the gas sample. If necessary, the analyzer 610 of mercury monitoring system produces a correction factor associated with the converter device for this concentration level.

After testing the second gas sample (e.g., 50% oxidized mercury to 50% elemental mercury) for the second time duration between time T3 and time T4, the mercury calibration subsystem 630 controls a flow rate of oxidizing component from source 640 so that the output of reaction chamber 628 includes a third set of concentrations of elemental mercury gas and oxidized mercury gas (e.g., 75% oxidized mercury to 25% elemental mercury) for a third duration of time between time T4 and time T5. For this third time duration, the mercury monitoring system 600 switches between delivering the gas sample on channel A and channel B to the detector 615 (as previously discussed) to identify an amount of elemental mercury and oxidized mercury present in the third gas sample. Based on measurements by the detector 615 during the third time duration, the mercury monitoring system 600 identifies whether converter efficiency falls below 100% for the given concentration of oxidized mercury (e.g., 7.5 micrograms/cubic meter) in the gas sample. If necessary, the mercury monitoring system produces a correction factor associated with the converter device for this concentration level.

Although graph 1400 illustrates three different testing ratios to check an efficiency associated with converter 625, note that any number of different sample gases including different ratios of elemental mercury gas to oxidized mercury gas can be used to verify the efficiency of the converter 625 over a range of different oxidized mercury concentrations.

Figure 21:
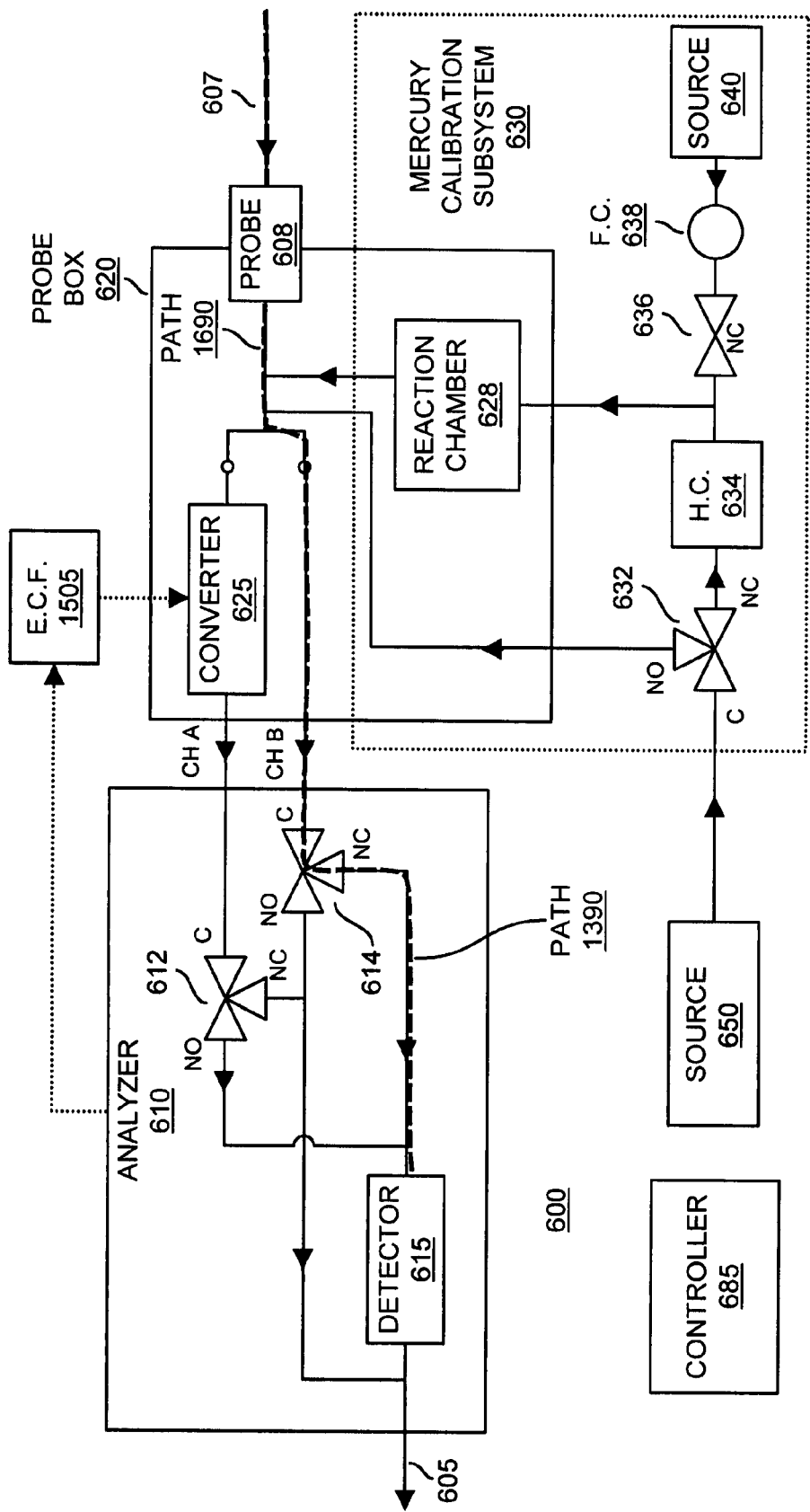

Passing the above integrity checks (e.g., detector calibration and converter efficiency) provides an assurance that the mercury monitoring system can properly detect mercury in a flue gas 607 sample. FIGS. 20 and 21 illustrate respective flow paths 1590 and 1690 in the mercury monitoring system 600 to measure a total amount of mercury present in the flue gas 607 (e.g., via a measurement on channel A or flow path 1590) and an amount of elemental mercury present in the flue gas 607 (e.g., via a measurement on channel B or flow path 1690). The techniques discussed above disclose how to produce different efficiency correction factors 1505. The different efficiency correction factors 1505 can be used to more accurately indicate a total amount of mercury present in a flue gas 607 sample.

For example, based on testing as discussed above, suppose that the converter 625 is: i) 98% efficient at converting oxidized mercury into elemental mercury for a concentration of 2.5 micrograms of mercury/cubic meter, ii) 97% efficient at converting oxidized mercury into elemental mercury for a concentration of 5.0 micrograms of mercury/cubic meter, and iii) 93% efficient at converting oxidized mercury into elemental mercury for a concentration of 7.5 micrograms of mercury/cubic meter. The corresponding efficiency correction factors would be 1.02, 1.03, and 1.08 for the different concentrations. In furtherance of the present example, via use of detector 615 and switching between measurements on channel A and channel B, suppose that the mercury monitoring system 600 detects a concentration of 5.6 micrograms/cubic meter of oxidized mercury and a concentration of 2.7 micrograms/cubic meter in flue gas 607. The efficiency correction factor of 1.03 is multiplied by 5.6 in order to identify an actual amount of oxidized mercury in the flue sample 607. The total mercury in the flue gas 607 would be (5.768+2.7) or 8.468 instead of (5.6+2.7), or 8.3 micrograms of mercury/cubic meter.

According to one configuration, a linear correction factor (as opposed to non-linear correction via application of different correction factors as discussed above for different ranges) such as a correction factor of 1.05 can be applied to all ranges of concentrations. This simplifies the conversion process because there is no need to determine a particular correction factor to be used for a given concentration range.

While this invention has been particularly shown and described with reference to preferred embodiments thereof, it will be understood by those skilled in the art that various changes in form and details may be made therein without departing from the spirit and scope of the invention as defined by the appended claims.

What is claimed is:

1. A system comprising:
    elemental mercury gas;
    an oxidizing agent gas;
    a chemical reaction chamber, the chemical reaction chamber including a porous, chemical reaction-enhancing medium through which to pass and react the elemental mercury gas and the oxidizing agent gas to produce a sample of oxidized mercury gas; and
    the chemical reaction chamber including an output to emit the sample of oxidized mercury gas produced by the chemical reaction-enhancing medium;
    a first input gas line from an elemental mercury gas source to the chemical reaction chamber, the first input gas line conveying the elemental mercury gas to the reaction chamber;
    a second input gas line from an oxidizing agent gas source to the chemical reaction chamber, the second input gas line conveying the oxidizing agent gas to the reaction chamber; and
    an elemental mercury gas humidifier disposed in the first input gas line between the elemental mercury gas source and the reaction chamber, the elemental mercury gas humidifier configured to humidify the elemental mercury gas passing through the first input gas line; and
    wherein the porous, chemical reaction-enhancing medium includes chemical reaction surface area sites in which to react humidified elemental mercury gas received from the first gas line and the oxidizing agent gas received from the second gas line;
    an elemental mercury detector;
    a first flow path from the output of the chemical reaction chamber to the elemental mercury detector, the first flow path including an oxidized mercury gas-to-elemental mercury gas converter; and
    a second flow path from the output of the chemical reaction chamber to the elemental mercury detector, the second flow path disposed to bypass the oxidized mercury gas-to-elemental mercury gas converter.

2. The system as in claim 1, wherein the porous, chemical reaction-enhancing medium is made of metal.

3. The system as in claim 1, wherein the porous, chemical reaction-enhancing medium is sintered metal.

4. The system as in claim 1, wherein the porous, chemical reaction-enhancing medium is sintered stainless steel.

5. The system as in claim 1, wherein surface areas of pores in the porous, chemical reaction-enhancing medium are coated with at least one of silica and glass.

6. The system as in claim 1, wherein the porous, chemical reaction-enhancing medium is a length of porous material disposed in the chemical reaction chamber; and
    wherein the chemical reaction chamber is configured to pass the received elemental mercury gas and the received oxidizing agent gas on a path through an outer surface of the porous material to a core of the porous material to the output of the chemical reaction chamber.

7. The system as in claim 1, wherein the porous, chemical reaction-enhancing medium is a length of porous material disposed in the chemical reaction chamber; and wherein the chemical reaction chamber is configured to pass the received elemental mercury gas and the oxidizing agent gas on a path through an inner surface of the porous material to an outer surface of the porous material to the output of the chemical reaction chamber.

8. The system as in claim 1, wherein the porous, chemical reaction-enhancing medium has a nominal pore size in a range between 0.1 micrometers and 500 micrometers.

9. The system as in claim 1 further comprising:
a chemical reaction-enhancing heater in thermal communication with the chemical reaction chamber to heat the received elemental mercury gas and the oxidizing agent gas in the chemical reaction chamber prior to passing of the elemental mercury gas and the oxidizing agent gas through the porous, chemical reaction-enhancing medium.

10. The system as in claim 9, wherein the chemical reaction chamber is configured to provide a thermally conductive path from the chemical reaction-enhancing heater through the chemical reaction chamber to the porous, chemical reaction-enhancing medium.

11. The system as in claim 10 further comprising:
an enclosure to house the chemical reaction-enhancing heater, the chemical reaction chamber, the first input gas line, and the second input gas line; and
the chemical reaction-enhancing heater configured to heat the chemical reaction chamber and the first input gas line and the second input gas line in the housing to preheat the elemental mercury gas in the first input gas line and the oxidizing agent gas in the second input gas line prior to entering the input of the chemical reaction chamber.

12. The system as in claim 1 further comprising:
a chemical reaction-enhancing heater in thermal communication with the chemical reaction chamber to heat the received elemental mercury gas and the oxidizing agent gas in the chemical reaction chamber prior to passing of the elemental mercury gas and the oxidizing agent gas through the porous, chemical reaction-enhancing medium; and
a controller configured to control an amount of heat produced by the chemical reaction-enhancing heater such that the received elemental mercury gas and the oxidizing agent gas are maintained at a temperature between 40 and 600 degrees Celsius.

13. The system as in claim 1, wherein the
an elemental mercury gas humidifier is configured to modify a relative humidity of the elemental mercury gas prior to being received by the chemical reaction chamber.

14. The system as in claim 13, wherein the elemental mercury gas humidifier is configured to control a relative humidity of the elemental mercury gas in a range between 40% and 100% relative humidity at a temperature in a range of 15-45 degrees Celsius.

15. The system as in claim 1 further comprising:
a gas generator that produces the elemental mercury gas based on evaporation of liquid mercury; and
wherein the chemical reaction chamber including the porous, chemical reaction-enhancing medium provides a back pressure of less than 4 pounds per square inch.

16. The system as in claim 1, wherein the chemical reaction chamber is configured to emit an unreacted portion of the elemental mercury gas and unreacted portion of the oxidizing agent gas that was not used to produce the oxidized mercury gas in the sample.

17. The system as in claim 1, wherein the porous medium has a nominal pore size in a range between 0.1 micrometers and 100 micrometers.

18. The system as in claim 1 further comprising:
a chemical reaction-enhancing heater in thermal communication with the chemical reaction chamber to heat the received elemental mercury gas and the oxidizing agent gas in the chemical reaction chamber prior to passing of the elemental mercury gas and the oxidizing agent gas through the porous medium; and
a controller configured to control an amount of heat produced by the chemical reaction-enhancing heater such that the received elemental mercury gas and the oxidizing agent gas are maintained at a temperature between 40 and 450 degrees Celsius.

19. The system as in claim 1, wherein the porous, chemical reaction-enhancing medium is a gas mixing device to mix the elemental mercury and the oxidizing agent gas.

20. The system as in claim 1, wherein the porous, chemical reaction-enhancing medium includes a heterogeneous surface reaction site in which to react the oxidizing agent gas with the elemental mercury gas.

21. The system as in claim 1 further comprising:
a flow controller with multiple different control settings to adjust an amount of the oxidizing agent gas inputted through the second input gas line to the chemical reaction chamber.

22. The system as in claim 1 further comprising:
a path selector system to select a path, from the first flow path and the second flow path, on which to convey the sample of oxidized mercury gas from the chemical reaction chamber to the elemental mercury detector.

23. The system as in claim 22 further comprising:
an analyzer in communication with the elemental mercury detector to verify i) an ability of the elemental mercury detector to properly detect a concentration of elemental mercury gas in the sample of oxidized mercury gas, and ii) an ability of the oxidized mercury gas-to-elemental mercury gas converter to convert oxidized mercury gas in the sample of oxidized mercury gas into elemental mercury gas.

24. The system as in claim 23 further comprising:
a probe to receive a flue sample gas;
a conduit on which to convey the flue sample gas from the probe to the first flow path and the second flow path; and
the path selector system including valves to i) selectively prevent conveyance of the oxidized mercury gas into the first flow path and the second flow path, and ii) switch between selecting the first flow path and the second flow path, on which to convey the flue sample gas to the elemental mercury detector.

25. The system as in claim 24 further comprising:
a chemical reaction-enhancing heater in thermal communication with the chemical reaction chamber to heat the received elemental mercury gas and the oxidizing agent gas in the chemical reaction chamber prior to passing of the elemental mercury gas and the oxidizing agent gas through the porous, chemical reaction-enhancing medium; and
a heater controller in communication with the chemical reaction-enhancing heater, the heater controller configured to control an amount of heat produced by the chemical reaction-enhancing heater such that the received element mercury gas and the oxidizing agent gas are maintained at a temperature between 40 and 600 degrees Celsius.

* * * * *